United States Patent [19]

Yoshida et al.

[11] 4,399,075

[45] Aug. 16, 1983

[54] PROCESS FOR PRODUCING CHLORINATED PHENOXYTOLUENE DERIVATIVES

[75] Inventors: Zenichi Yoshida, Kyoto; Susumu Kato, Sakai; Takuya Fujiki, Kyoto; Yasuhiro Amemiya, Hirakata, all of Japan

[73] Assignee: Asahi Chemical Company, Limited, Japan

[21] Appl. No.: 277,347

[22] Filed: Jun. 25, 1981

[51] Int. Cl.[3] .............................................. C07C 41/22

[52] U.S. Cl. ............................... 260/465 F; 568/639; 568/637; 568/585; 568/586; 568/313; 560/55; 560/138

[58] Field of Search ................ 570/196, 197; 568/639, 568/637, 585, 586, 316; 260/465 F; 560/55, 138

[56] References Cited

U.S. PATENT DOCUMENTS

| | | | |
|---|---|---|---|
| 2,430,822 | 11/1947 | Nevison | 570/196 |
| 2,844,635 | 7/1958 | Mayor | 570/196 |
| 3,363,013 | 1/1968 | Kyker | 570/197 |
| 4,014,940 | 3/1977 | Ume et al. . | |
| 4,085,147 | 4/1978 | Rosinger et al. . | |
| 4,092,369 | 5/1978 | Gelfand | 570/197 |
| 4,108,904 | 8/1978 | Brown et al. . | |
| 4,146,737 | 3/1979 | Sheldon et al. . | |

FOREIGN PATENT DOCUMENTS

| | | |
|---|---|---|
| 2707232 | 8/1978 | Fed. Rep. of Germany . |
| 2010837 | 6/1979 | United Kingdom . |

OTHER PUBLICATIONS

Derwent Print Commands, J55089237-C34 published Jul. 5, 1980.

*Primary Examiner*—Bernard Helfin
*Attorney, Agent, or Firm*—Larson and Taylor

[57] ABSTRACT

Phenoxytoluene derivative is chlorinated in a very high yield and selectivity in the presence of nitrogen-, sulfur-, phosphorus- or oxygen-containing compound which is capable of forming a charge-transfer complex with chlorine, chlorine radical or organic halogen compound, together with radical initiator and organic halogen compound.

14 Claims, No Drawings

PROCESS FOR PRODUCING CHLORINATED PHENOXYTOLUENE DERIVATIVES

This invention relates to a process for producing chlorinated phenoxytoluene derivatives in high yields and selectivities by chlorinating a methyl group on a side chain of phenoxytoluene derivatives. The chlorinated phenoxytoluene derivatives of this invention include both phenoxybenzyl chlorides and phenoxybenzal chlorides. These chlorinated phenoxytoluene derivatives are easily converted by hydrolysis to phenoxybenzyl alcohol derivatives or phenoxybenzaldehyde derivatives. Especially, m-phenoxybenzyl alcohol or m-phenoxybenzaldehyde is an important intermediate of agricultural chemicals and insecticides. Various processes have heretofore been reported for producing phenoxybenzyl alcohols and phenoxybenzaldehydes.

For example, several patents have already been filed on processes for producing chlorinated phenoxytoluene derivatives by chlorinating methyl group in a side chain of phenoxytoluene derivatives, which processes are deemed to be preferable industrially.

1. Japanese Published Examined Patent Application (Kokoku) Nos. 10,228/1976 and 45,573/1976 (U.S. Pat. No. 4,014,940) discloses a method of chlorinating directly m-phenoxytoluene with use of phosphorus halogenide at a high temperature of more than 220° C. This method, however, has an disadvantage of accompanying a reaction operation at a high temperature and consumption of a lot of energy. Moreover, in this process, selectivities are low in both phenoxybenzyl chlorides and phenoxybenzal chlorides and especially low in phenoxybenzal chlorides.

2. Japanese Published Unexamined Patent Application (Kokai) No. 95,623/1977 (U.S. Pat. No. 4,085,147) discloses the preparation of a mixture of m-phenoxybenzyl chloride and m-phenoxybenzal chloride by chlorinating m-phenoxytoluene with chlorine in carbon tetrachloride in the presence of a radical initiator. This process gives the contemplated products in rather low selectivities. Especially, selectivity of phenoxybenzal chloride is very low with accompanying a production of a lot of nuclear-chlorinated products.

3. Japanese Kokai No. 40,732/1978 (U.S. Pat. No. 4,108,904) describes halogenation of m-phenoxytoluene by use of sulfuryl chloride, chlorine or bromine as a halogenating agent in carbon tetrachloride. The process is carried out with use of a free radical initiator or a strong incandescent light source. However, selectivities are rather low in both m-phenoxybenzyl chloride and m-phenoxybenzal chloride and especially very low in m-phenoxybenzal chloride.

4. Japanese Kokai No. 46,929/1978 (U.S. Pat. No. 4,146,737) discloses a method of chlorinating m-phenoxytoluene on the side chain in carbon tetrachloride with use of sulfuryl chloride as a halogenating agent in the presence of a radical initiator. In this method, the contemplated products are obtained in rather low selectivities and m-phenoxybenzal chloride in very low selectivity.

5. Japanese Kokai No. 103,433/1978 (DT-OS No. 27 07 232) shows a halogenation of m-phenoxytoluene on the side chain in carbon tetrachloride with chlorine or bromine as a halogenating agent by use of ultraviolet rays. In this process, selectivities are also low. When phenoxybenzal halide is obtained in a rather high selectivity, a highly chlorinated trichloride derivatives are produced in a large amount.

6. Japanese Kokai No. 92,928/1979 (U.K. patent application No. 2,010,837 describes a process for preparing m-phenoxybenzyl chloride, which comprises reacting m-phenoxytoluene with chlorine in the presence of a sulphur-containing catalyst without using a radical initiator and at a temperature which is, or is equivalent to, 200° to 280° C. at atmospheric pressure. However, selectivity of m-phenoxybenzyl chloride is rather low and that of m-phenoxybenzal chloride is extremely low.

It is generally known that, in the chlorination of aromatic compounds, electrophilic substitution reactions in the benzene ring proceed in competition with radical substitution reactions on the side chain. This occurs also in the chlorination of phenoxytoluene derivatives. For example, in U.S. Pat. No. 4,085,147, it is shown that a lot of nuclear-chlorinated products are formed together with side chain-chlorinated products.

Further, phenoxybenzal chloride derivatives are converted to phenoxyphenyl trichloromethane derivatives with a progress of chlorination. Accordingly, it is necessary to restrict the formation of the trichloride derivatives simultaneously with the restriction of the chlorination in benzene ring in order to obtain phenoxybenzal chloride derivatives in an high yield and high selectivity.

An object of this invention is to provide a method of chlorinating a phenoxytoluene derivative on the side chain in an extremely high yield and high selectivity.

An object of this invention is to provide a method of chlorination of a phenoxytoluene derivative with accompanying a very small formation of nuclear-chlorinated products and phenoxyphenyl trichloromethane derivatives.

Another object of this invention is to provide a method of chlorinating a phenoxytoluene derivative in which each of phenoxybenzyl chloride and phenoxybenzal chloride derivative is obtained in a very high yield and high selectivity.

These and other objects of the invention will become apparent from the following description.

The present invention provides a process for preparing a chlorinated phenoxytoluene derivative represented by the formula

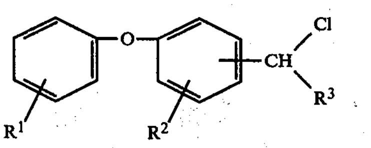

(1)

wherein $R^1$ and $R^2$ are the same or different and are each hydrogen, halogen, cyano, nitro, alkyl, alkoxyl, alkoxycarbonyl, halogenoalkyl, acyl, acyloxy, aryl, aralkyl or aralkyloxy, $R^3$ is hydrogen or chlorine, characterized by chlorinating with chlorine a phenoxytoluene derivative represented by the formula

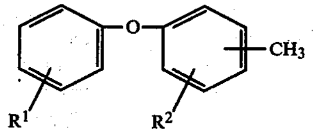

(2)

wherein $R^1$ and $R^2$ are same as above, in the presence of at least one compound selected from the group consisting of nitrogen-containing compound, sulfur-containing compound, phosphorus-containing compound and oxygen-containing compound which is capable of forming a charge-transfer complex with chlorine, chlorine radical or organic halogen compound, together with radical initiator and organic halogen compound.

According to this invention, both of phenoxybenzyl chloride derivatives and phenoxybenzal chloride derivatives are prepared in an extremely high yield and high selectivity compared with the afore-mentioned conventional processes. Nuclear-chlorinated products and phenoxyphenyl trichloromethane derivatives, by-products, are restricted in an amount of usually less than 2 to 3%, respectively. These findings are quite novel which are not seen in conventional processes.

The chlorinated phenoxytoluene derivatives obtained by the present process are represented by the formula (1). In the groups $R^1$ to $R^2$, preferable examples of halogen are chlorine and bromine. Preferable examples of alkyl are those having 1 to 4 carbon atoms such as methyl, ethyl and butyl. Examples of preferable alkoxyl are those having 1 to 4 carbon atoms such as methoxy and propoxy. Examples of alkoxycarbonyl are those having 2 to 5 carbon atoms such as methoxycarbonyl and butoxycarbonyl. Halogenoalkyl has preferably 1 to 4 carbon atoms and includes for example chloromethyl and bromoethyl. Preferable examples of the group acyl both in acyl and acyloxy are those having 2 to 8 carbon atoms such as acetyl, propionyl, benzoyl and toluoyl. Examples of preferable aryl are those having 6 to 9 carbon atoms such as phenyl, tolyl and xylyl. Preferable examples of the group aralkyl both in aralkyl and aralkyloxy are those having 7 to 10 carbon atoms such as benzyl, phenylethyl and phenylpropyl.

Nitrogen-containing compounds useful in this invention are a wide variety of compounds represented by the following formulae.

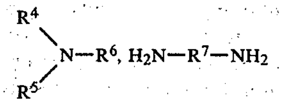

Preferable examples of $R^4$ to $R^6$ are hydrogen; alkyl having 1 to 20 carbon atoms such as methyl, butyl, octyl, dodecyl, hexadecyl, stearyl, etc; hydroxyalkyl having 1 to 10 carbon atoms such as hydroxymethyl, hydroxypropyl, hydroxyheptyl, etc; cycloalkyl having 5 to 8 carbon atoms such as cyclohexyl, cycloheptyl etc; aryl having 6 to 10 carbon atoms with or without a substituent such as phenyl, tolyl, ethylphenyl, chlorophenyl, trichlorophenyl, bromophenyl, etc. Two or three of $R^4$ to $R^6$ may form a ring.

Preferable examples of $R^7$ are alkylene having 2 to 8 carbon atoms such as ethylene, propylene, hexamethylene, etc; arylene having 6 to 10 carbon atoms such as phenylene, tolylene, dimethylphenylene, chlorophenylene, etc.

Examples of preferable nitrogen-containing compounds are triethylamine, isobutylamine, 1-methylpentylamine, di-n-octylamine, n-dodecylamine, n-hexadecylamine, stearylamine, diethanolamine, cyclohexylamine, aniline, N,N-diethylaniline, 2,4,5-trichloroaniline, p-toluidine, hexamethylenediamine, p-phenylenediamine, succinimide, piperidine, pyridine, quinoline, 2-imidazoline, ethyleneimine, hexamethylenetetramine, 3,5-di-n-heptyl-1,2,4-triazole, 2,4-di-(4-pyridyl)-6-methyl-s-triazine, 1,8-diazabicyclo(5,4,0)-7-undecene, 1,4-diazabicyclo(2,2,2)octane, etc.

Useful sulfur-containing compounds of the invention are represented by the following formulae.

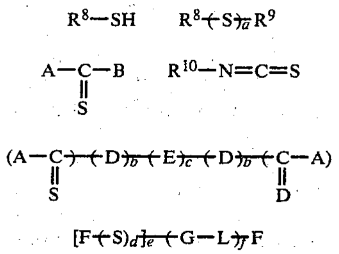

Preferable examples of $R^8$ and $R^9$ are alkyl having 1 to 20 carbon atoms; cycloalkyl having 5 to 8 carbon atoms; aryl having 6 to 10 carbon atoms; heterocyclic group having nitrogen, sulfur, oxygen atom, etc. Further $R^8$ and $R^9$ may conjointly form an alicyclic or heterocyclic ring, a is an integer of 1 to 8. A and B is $R^{11}$, $NR^{12}R^{13}$, $NR^{12}NR^{12}R^{13}$, $NR^{12}NCR^{12}R^{13}$, $SR^{12}$, $SNR^{12}R^{13}$, $SHNR^{12}R^{13}R^{14}$ or $OR^{14}$, $R^{10}$ to $R^{14}$ are hydrogen, alkyl having 1 to 20 carbon atoms, aryl having 6 to 10 carbon atoms, alicyclic or heterocyclic ring and $R^{12}$ and $R^{13}$ or $R^{12}$ to $R^{14}$ may conjointly form a heterocyclic ring. $R^{12}$ and $R^{13}$ further include acyl having 1 to 20 carbon atoms with or without a substituent and $R^{11}$ does not include hydrogen. A and B may conjointly form an alicyclic or heterocyclic ring. D is $NR^{12}$, sulfur atom or oxygen atom, E is $R^{15}$, $R^{15}SR^{15}$, $R^{15}SO_2R^{15}$, $C(S)NHR^{15}NHC(S)$, $R^{15}NHC(S)NHR^{15}$, $R^{15}NR^{12}R^{15}$, $R^{15}C(O)R^{15}$ or $R^{15}C(S)R^{15}$, b is 0 or an integer of 1 to 4 but b is 1 when D is $NR^{12}$ or oxygen atom, c is 0 or 1. F is $R^{16}$, CN, $NR^{17}R^{18}$, $C(O)R^{17}$, $S(O)R^{17}$, $C(O)OR^{17}$, $C(O)NR^{17}R^{18}$, $C(O)SR^{17}$, $R^{19}C(O)OR^{17}$, $R^{19}C(O)NR^{17}R^{18}$, $R^{19}SR^{17}R^{19}NR^{17}R^{18}$, $R^{19}C(O)R^{17}$ or $HNR^{17}R^{17}R^{18}$, $R^{16}$ to $R^{18}$ are hydrogen; alkyl having 1 to 20 carbon atoms, aryl having 6 to 10 carbon atoms, alicyclic or heterocyclic group with or without a substituent; but $R^{16}$ is alkyl, aryl or alicyclic group having a substituent when f is 0, $R^{19}$ is alkylene having 1 to 12 carbon atoms or arylene having 6 to 10 carbon atoms with or without a substituent. G is $R^{19}$, $R^{19}C(O)R^{19}$, $C(O)R^{19}C(O)$ or C(O), L is sulfur atom or $NR^{17}$, d is 1 to 8, e is 1 to 50 and f is 0 or 1 to 50, and F further includes $R^{19}OR^{17}$ and $R^{19}OR^{19}OR^{19}$ when d is other than 1. In the above, as the groups alkyl, cycloalkyl, aryl, alkylene and arylene, the same are usable as those described in the nitrogen-containing compounds. As the acyl group in the definition of the above A and B, acetyl, butyryl, stearoyl, benzoyl, toluoyl and like acyl groups are enumerated.

Preferable examples of sulfur-containing compounds are isobutyl mercaptan, n-octyl mercaptan, n-dodecyl mercaptan, n-hexadecyl mercaptan, stearyl mercaptan, cyclohexyl mercaptan, thiophenol and like mercaptans; diisopropyl sulfide, di-n-octyl sulfide, di-n-dodecyl sulfide, di-n-hexadecyl sulfide, distearyl sulfide, diphenyl sulfide, dicyclohexyl sulfide, 2,2′-dipyridyl sulfide and like monosulfides; di-tert-butyl disulfide, di-n-octyl disulfide, di-n-dodecyl disulfide, di-n-hexadecyl disulfide, distearyl disulfide, diphenyl disulfide, dicyclohexyl disulfide, 2,2′-benzothiazolyl disulfide, diethyl tetrasulfide and like polysulfides; 2-mercaptobenzothiazole, tetrahydrothiophene, thiophene, 2-n-dodecyl-1,3,5-trithiane, 2-phenyl-1,3-dithian, 4-methylthiacyclohexane and like cyclic sulfur compounds; methyl cyclohexyl thioketone, 4,4'-bis(N,N-dimethylamino)thiobenzophenone, cyclohexanethion, 1-(n-heptadecyl)-2-thiourea, 1-isopropyl-3-(n-dodecyl)-2-thiourea, 1-(n-dodecanoyl)-2-thiourea, 1,3-dicyclohexyl-2-thiourea, 1-(p-tolyl)-3-(2-pyridyl)-2-thiourea, 1,1,3,3-tetra-n-propyl-2-thiourea, 1,4-diethyl-1,4-diphenyl-3-thiosemicarbazide, 1-isonicotinoyl-4-(n-octadecanoyl)-3-thiosemicarbazide, 1-(n-dodecanoyl)-4-(p-isoamyloxyphenyl)-3-thiosemicarbazide, 1-ethoxycarbonylmethyl-1-phenyl-4-ethyl-3-thiosemicarbazide, 1-(n-heptadecyl)-4-thiosemicarbazone, 1-(3-pyridyl)-5-ethyl-4-thiosemicarbazone, 1-pentamethylene-4-thiosemicarbazone, 1,5-diphenyl-3-thiocarbohydrazide, dithizone, 1,1,7,7-tetraphenyl-4-bis-thiocarbohydrazone, 1,7-di-n-heptadecyl-4-bisthiocarbohydrazone, 1,7-dipentamethylene-4-bisthiocarbohydrazone, 5-ethyl-2-thiobiuret, 5-phenyl-1-(p-chlorophenyl)-2-thiobiuret, 5-(n-propyl)-2,4-dithiobiuret, N,N',N'',N'''-hexamethylguanyl thiourea, 1-benzoyl-2-guanyl thiourea, thioacetanilide, thiobenzamide, thiobenzanilide, n-heptadecylthioamide, N-cyclohexylthiobenzamide, 2-benzothiazolylethyl thioanilide, thiophenylacetohydrazide, methylphenylthio-n-valerohydrazone, 2,4-dichlorophenylthiophenylacetohydrazone, N-(n-octyl)-N-aminoethyl dithiocarbamic acid, n-heptadecyl dithiocarbamic acid n-heptadecylammonium salt, 2-thiazolyldithiocarbamic acid triethylammonium salt, N-pentamethylene dithiocarbamic acid piperidinium salt, cyclohexyldithiocarbamic acid cyclohexylammonium salt, N,N-dimethyl S-(n-hexadecyl)dithiocarbamate, N,N-dimethyl S-(2-benzothiazolyl)dithiocarbamate, N-pentamethylene S-mercaptoethyl dithiocarbamate, N-diethyleneoxy S-hydroxyethyl dithiocarbamate, O-cyclohexylthioncarbamate, N-carboxymethyl O-(n-hexadecyl)thioncarbamate, N-pentamethylene O-(n-propyl)thioncarbamate, diethyl dithiocarbamyl sulfenamide, methylphenyl dithiocarbamyl sulfenamide, benzyl thionpropionate, methylthion cyclohexane carboxylate, isoamyl p-thiontoluate, dithiobenzoic acid, ethyl dithio-n-heptanoate, n-butyl dithiocyclohexanecarboxylate, carboxymethyldithio acid phenylacetate, n-dodecyl phenylthioncarbonate, tetramethylenethioncarbonate, diphenylthioncarbonate, di-n-octadecyl trithiocarbonate, di-n-dodecyl trithiocarbonate, di(4-chlorophenyl)trithiocarbonate, dicyclohexyl trithiocarbonate, S,O-(di-n-dodecyl)xanthate, S-carboxydecamethylene O-(n-dodecyl)xanthate, S-(n-hexadecyl) O-cyclohexyl xanthate, S-lauroyl O-ethylxanthate, O-cyclohexylthion carbazate, 1-(n-dodecylidene) O-ethylthioncarbazate, 1-(n-dodecylidene) S-ethyldithiocarbazate, isobutyl isothiocyanate, n-octyl isothiocyanate, cyclohexyl isothiocyanate, p-(N,N-dimethylamino)phenyl isothiocyanate, 6-isothiocyanoquinoline, isothiocyanocapric acid methyl ester, ethylene diisothiocyanate, hexamethylene diisothiocyanate, methylenebis(N,N-dimethyldithiocarbamate), p-xylylenebis(N,N-dimethyldithiocarbamate), N,N-bis(N',N'-dimethylthiocarbamoylthioethyl)methylamine, bis(N,N-dimethylthiocarbamoylthioethyl)sulfide, p,p'-bis(dithiocarbamoyl)diphenyl sulfone, 1,4-phenylenebisisopropyl thiourea, dimethylene trithiourea, methylenebistetramethylene thiourea, bis(N-trimethylenethioacetamide), ethylenebisdithiocarbamic acid diammonium salt, diisopropyldithion oxalate, S,S'-diethyl O,O'-decamethylenebisxanthate, O,O'-dicyclohexyl S,S'-methylenebisxanthate, O,O'-di(n-octyl) S,S'-(p-xylylene)bisxanthate, cyclohexylxanthogene monosulfide, ethoxyethylxanthogene monosulfide, n-hexadecyl dixanthogene, benzyl dixanthogene, ethyl dixanthogene disulfide, O-ethylthiooxalamide, N,N'-dimorpholinodithiooxalic diamide, N,N-di(n-dodecyl)-dithiooxalic diamide, N,N'-diphenyldithio(n-butyl)malonic diamide, N,N'-di-n-octyldithioadipic diamide, bis(piperidinothiocarbonyl)monosulfide, bis(morpholinothiocarbonyl)monosulfide, bis(hydrazinothiocarbonyl)monosulfide, bis(n-octylidenehydrazinothiocarbonyl)monosulfide, bis(di-n-butylthiocarbamoyl)disulfide, bis(piperidinothiocarbonyl)disulfide, bis(morpholinothiocarbonyl)disulfide, ethylene-1,2-bis[1,2-(dithiocarbamoyl)ethylene]disulfide, ethylene-1,2-bis(benzothiazolylthiocarbamoyl)disulfide, bis(dimethylthiocarbamoyl)tetrasulfide, bis(piperidinothiocarbonyl)hexasulfide, n-octadecyl thiocyanate, pentamethylene dithiocyanate, 2-chlorocyclohexyl thiocyanate, p-aminophenyl thiocyanate, 3-thiocyanopyridine, N-diethyleneoxy-2-benzothiazolyl sulfenamide, N-(n-heptadecyl)-n-octyl sulfenamide, N-tert-butyl-2-benzothiazolyl sulfenamide, N-cyclohexyl-2-benzothiazolyl sulfenamide, di-n-amyl thiosulfinate, tert-butylethyl thiosulfinate, thiostearic acid, thioterephthalic acid, cyclohexylthiol acetate, N,N-diethylaminoethylthiolphenylacetate, dicyclohexyldithiosebacate, 1,6-hexamethylenedithiol diacetate, S-phenacyl O-ethylthiolcarbonate, S,S'-dimethylenecarboxy O,O'-diethylbisthiolcarbonate, diphenyl dithiolcarbonate, N-(ζ-aminohexamethyl)thiocarbamic acid, N-phenylthiocarbamic acid, N-stearylthiocarbamic acid stearylammonium salt, N-isobutylthiocarbamic acid isobutylammonium salt, N-pentamethylene S-phenylthiol carbamate, N-cyclohexyl S-pentamethylenethiol carbamate, S,S'-pentamethylenebisthiol carbamate, n-hexylmercaptocapric acid, 2-thienylmercaptoacetic acid, n-octadecylmercaptosuccinic acid diethyl ester, 2-thienylmercaptoacetic acid n-dodecyl ester, methylmercaptopelargonic acid amide, n-octylmercaptobenzamide, S,S'-di(n-octadecyl)methyl thioacetal, S,S'-dibenzylcyclohexyl ketone thioacetal, ethylenebis(S,S'-di-n-octadecylmethyl)ketone thioacetal, tri-n-dodecyl trithioorthoformate, triphenyltrithioorthobenzoate, tetraisopropyl tetrathioorthocarbonate, tetracyclohexyl tetrathioorthocarbonate, di(β-chloroethyl)sulfide, 1,10-decamethylenebischloroethyl sulfide, γ-chloro-γ'-(N,N-diethylamino)dipropyl sulfide, N-(n-octadecyl)iminomethylethyl sulfide, di(N-pentamethyleneaminoethyl)sulfide, n-butylmercaptoacetaldehyde, p-benzylmercaptobenzaldehyde, n-dodecylmercaptomethyl phenyl ketone, bis(n-heptylcarbonylmethyl)sulfide, n-octadecylmercaptopropionitrile, di(chloroacetyl)sulfide, dibenzoyl sulfide, ethylenebis(β-cyanoethyl sulfide), 1,18-octadecamethylene bis(n-octadecyl sulfide), bis{2-[2-(2-chloroethylthio)ethylthio]ethyl}sulfide, poly(ethylenesulfide), poly(phenylenesulfide), α,α'-di-n-hexadecyl-di(carboxymethyl)disulfide, di(κ-carboxydecyl)disulfide, di(cyclohexyloxycarbonylethyl)disulfide, di(n-octadecyloxycarbonylethyl)disulfide, di(N-methyolanilinocarbonylmethyl)disulfide, di(γ-carbamoylpropyl)disulfide, di(ζ-chlorohexyl)disulfide, di(2,4-dichlorophenyl)disulfide, di(N,N-dimethylaminohexamethyl)disulfide, di(m-aminophenyl)disulfide, di(α-formylisopropyl)disulfide, di(o-formylmethylthiophenyl)disulfide, di(methylcarbonylisobutyl)disulfide, di(2-methylcarbonyl-5-methoxyphenyl)disulfide, di(p-cyanophenyl)disulfide, ζ-cyano-ζ'-hydroxy dihexamethyl disulfide, dibenzoyl disulfide, di-3-nicotinoyl disulfide, poly(ethylformal disulfide), poly(ethylene disulfide), di(γ-hydroxypropyl)disulfide, di(m- hydroxyphenyl)disulfide, di($\beta$-ethoxyethyl)disulfide, di(2-ethoxy-1-naphthyl)disulfide, di(carboxymethyl)trisulfide, di(o-carboxyphenyl)tetrasulfide, di(p-ethoxycarbonylphenyl)trisulfide, di(n-dodecyloxycarbonylmethyl)tetrasulfide, di(carbamoylmethyl)trisulfide, di(o-n-butylcarbamoylphenyl)tetrasulfide, di($\beta$-chloroethyl)tetrasulfide, di($\beta$-chloroethyl)pentasulfide, di(p-aminophenyl)trisulfide, di(ethylenediaminoethyl)tetrasulfide, di($\beta$-formylethyl)trisulfide, di(m-formylphenyl)trisulfide, di(acetylmethyl)trisulfide, di(3-acetyl-4-hydroxy-1-naphthyl)trisulfide, di($\beta$-cyanoethyl)trisulfide, di(p-cyanophenyl)trisulfide, dibenzoyl tetrasulfide, diacetyl tetrasulfide, poly(ethylene pentasulfide), poly(oxydiethylene tetrasulfide), di($\beta$-hydroxyethyl)trisulfide, di(2-hydroxy-1-naphthyl)trisulfide, di(n-dodecyloxyethyl)trisulfide, di(2-ethoxy-1-naphthyl)trisulfide, $\alpha$-mercaptostearic acid, $\kappa$-mercaptoundecylic acid, n-octadecyl mercaptoacetate, ethyl mercaptosuccinate, methyl p-mercaptobenzoate, $\alpha$-mercaptopropionanilide, $\epsilon$-mercaptocaproic acid amide, 2,3-dichloropropyl mercaptan, pentachlorothiophenol, $\beta$-mercaptoethyl n-dodecylamine, N,N-di($\gamma$-mercaptoisobutyl)piperazine, $\beta$-formylethyl mercaptan, $\alpha$-phenyl-$\beta$-formylethyl mercaptan, di(p-mercaptophenyl)ketone, mercaptomethyl n-hexyl ketone, $\beta$-cyanoethyl mercaptan, p-cyanothiophenol, bis(ethylenedimercaptomethyl)methane, 2-n-heptylmercaptocyclohexanethiol, di($\beta$-mercaptoethyl)disulfide, p-hydroxy-p'-mercaptodiphenyl disulfide, di(2-mercapto-1-naphthyl)trisulfide, di($\beta$-mercaptoethyl)tetrasulfide, 1,6-hexamethylene dithiol, 1,18-octadecamethylene dithiol, 1,2-cyclohexane dithiol, 3,4-thiophene dithiol, etc.

Phosphorus-containing compounds employed in the invention are represented by the following formulae.

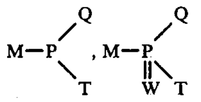

Preferable examples of M, Q and T are hydrogen, halogen, $R^{20}$, $WR^{20}$ or $NR^{20}R^{21}$, $R^{20}$ and $R^{21}$ are the same or different and are hydrogen, alkyl having 1 to 20 carbon atoms; aryl having 6 to 10 carbon atoms; amino; alicyclic or heterocyclic ring, W is oxygen atom or sulfur atom, and M and Q, or Q and T may conjointly form an alicyclic or heterocyclic ring, and at least two of M, Q and T are organic group other than hydrogen. In the above, examples of halogen are chlorine, bromine, etc. As the groups alkyl and aryl, the same are usable as those described in the nitrogen-containing compounds.

Examples of preferable phosphorus-containing compounds are tri-n-butylphosphine, tri-n-octylphosphine, tri-n-dodecylphosphine, n-octadecyldiphenylphosphine, triphenylphosphine, 1-mercaptoethyldiphenylphosphine, tricyclohexylphosphine, dicyclohexyl 4-chlorophenylphosphine, triisopropylphosphine sulfide, n-hexadecyldiphenylphosphine sulfide, triphenylphosphine oxide, tri-n-dodecylphosphine oxide, N,N-diethylhydrazinodiphenylphosphine oxide, 1-phenyl-1-phosphacyclohexane, n-octadecyl diphenyl phosphite, dicyclohexyl chloro phosphite, di-n-octyl phosphite, diphenyl cyclohexyl phosphite, triphenyl phosphite, tricyclohexyl phosphite, diiosopropyl chloro thiophosphite, tricyclohexyl thiophosphite, tri-n-dodecyl thiophosphite, triphenyl thiophosphite, tris(dimethylamino)phosphine, phosphorus tripiperidide, tris(di-n-butylamino)phosphine, phosphorus tri(N-methylanilide), diphenylphosphinic chloride, cyclohexylphenylphosphinothioic chloride, di-n-butylphosphinothioic acid, isopropyl n-hexyl phosphinic acid, dicyclohexylphosphinodithioic acid, methyl n-octyl n-hexyl phosphinate, O-methyl diisopropylphosphinothioate, phenyl diethylphosphinodithioate, methyl dicyclohexyl phosphinate, hexamethylene phosphoric triamide, phenyl phosphonus dichloride, cyclohexylphosphonic dichloride, S,S-diethyl phenylphosphonodithioate, diethyl-n-butylphosphonate, O,O-diethyl phenylphosphonothioate, O,S-diethyl phenylphosphonothioate, S-ethyl N,N-diethyl P-methyl phosphonamide thioate, O-ethyl phenyl phosphonodithioate, O-ethyl S-phenyl phenylphosphonodithioate, etc.

Useful oxygen-containing compounds of this invention are represented by the following formulae.

$$R^{22}—OH,\ R^{22}—O—R^{23},\ X[(R^{24}—O)_g(R^{25}—Z)_hR^{24}—Y]_i$$

Preferable examples of $R^{22}$ and $R^{23}$ are alkyl having 1 to 20 carbon atoms, aryl having 6 to 10 carbon atoms, alicyclic of heterocyclic ring, and $R^{22}$ and $R^{23}$ may form an alicyclic, heterocyclic or large polyether ring. $R^{24}$ and $R^{25}$ are the same or different and are alkylene having 2 to 8 carbon atoms, X is hydrogen atom, sulfur atom, alkoxyl, alkylamino or alkylamido, each having 1 to 20 carbon atoms and with or without a substituent, aryloxy having 6 to 10 carbon atoms, oxyalicyclic or oxyheterocyclic ring, each having or not having a substituent, Y is hydrogen, halogen, hydroxyl, mercapto, alkyl having 1 to 20 carbon atoms, carboxylalkyl having 2 to 20 carbon atoms or alkylamino having 1 to 20 carbon atoms, Z is oxygen atom or sulfur atom, g is 1 to 50, h is 0 to 25 and i is 1 to 6 but i is 2 when X is oxygen atom or sulfur atom. In the above, as halogen, alkyl, aryl, alkyl in the groups alkoxyl, alkylamino, alkylamido and carboxyalkyl, aryl in the group aryloxy, the same are usable as those in the aforementioned nitrogen- or sulfur-containing compounds. Examples of oxyalicyclic and oxyheterocyclic ring are cyclohexyloxy, pyridyloxy, quinolyloxy, etc. In the invention are excluded ethers having boiling point of less than 70° C.

Preferable examples of oxygen-containing compounds are 2,2'-dichlorodiethyl ether, di-n-butyl ether, di-n-octyl ether, di-n-octadecyl ether, diphenyl ether, naphthyl ethyl ether, dicyclohexyl ether, 4-pyridyl ethyl ether, p-dioxane, furan, tetrahydrofuran, 15-crown-5, dibenzo-18-crown-6, isobutyl alcohol, n-octyl alcohol, n-tetradecyl alcohol, n-octadecyl alcohol, m-cresol, 2,6-di-tert-butyl-4-methyl phenol, 2-(3-tolyoxy)-3-methyl phenol, 2,2'-methylenebis(4-methoxy-6-tert-butyl phenyl), 4,4'-thiobis(3-methyl-6-tert-butyl phenol), 4-hydroxypyridine, cyclohexyl alcohol, ethylene glycol, ethylene dithioglycol, ethylene glycol mono-n-butyl ether, diethylene glycol mono-n-dodecyl ether, propylene glycol diisopropionate, tripropylene glycol monostearate, ethylene glycol monophenyl ether, $\beta$-cyclodextrin, 1,5-sorbitan monostearate, glycerin monopalmitate, bis(hydroxyethylthioethyl)ether, bis(-mercaptoethylthioethyl)ether, bis(chloroethoxyethyl)ether, bis(aminoethylthioethyl)ether, ethylene dithioglycol hexamer, polyethylene glycol, polypropylene glycol, polyoxyethylene 1,5-sorbitan monostearate, polyoxyethylene glycerin monoplamitate, polyoxyethylene dodecyl ether, polyoxyethylene p-dodecylphenyl ether, polyoxyethylene laurylamine, polyoxyethylene laurylamide, etc.

In this invention, the above-mentioned nitrogen-, sulfur-, phosphorus- and oxygen-containing compounds are capable of forming charge-transfer complex with chlorine, chlorine radical or organic halogen compounds. These N, S, P and O-containing compounds are usable singly or at least two of them are usable, and are used in an amount of about 0.001 to 50 wt %, preferably about 0.01 to 30 wt % based on the starting phenoxytoluene derivative. With use of the above-mentioned range of the compound, the contemplated reaction proceeds effectively.

Examples of useful organic halogen compounds are represented by the formulae below.

$CH_m(Hal)_{4-m}$, $CH_{m'}(Hal)_{3-m'}CH_{m'}(Hal)_{3-m'}$, $CH_{m''}(Hal)_{2-m''}=CH_{m''}(Hal)_{2-m''}$, 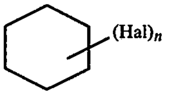

In the above, Hal means halogen atom such as chlorine, bromine, iodine, etc., m is 0 or an integer of 1 to 3, m' is 0 or an integer of 1 to 2, m" is 0 or 1, n is an integer of 1 to 6.

Preferable examples of organic halogen compounds are carbon tetrachloride, carbon tetrabromide, carbon tetraiodide, chloroform, bromoform, iodoform, methylene chloride, methylene bromide, dichloroethane, trichloroethane, tetrachloroethane, tetrachloroethylene, hexachlorocyclohexane, etc. Chlorinated paraffin is also included in organic halogen compound of the invention. More preferable organic halogen compound are carbon tetrachloride and carbon tetrabromide. These organic halogen compounds are usable singly or at least two of them are usable, and are used in an amount of usually 1 to 20 times, preferably 5 to 10 times the weight of the starting phenoxytoluene derivative.

Useful radical initiators of the invention are azo compounds or peroxides, and preferably are azobisisobutyronitrile, benzoyl peroxide, etc. The radical initiator is used in an amount of usually about 0.001 to 20 wt %, preferably about 0.01 to 15 wt % of the phenoxytoluene derivative. It is preferable to blow chlorine into the reaction system in an amount of about 0.5 to 10 mole %, preferably about 2 to 5 mole % of the phenoxytoluene derivative in a minute until the reaction is completed. The reaction is conducted at usually about 0° to 150° C., preferably at a temperature of reflux state of the reaction mixture.

The desired compound of the invention is easily purified by known methods such as concentration, extraction, distillation, recrystallization, column chromatography, etc.

The invention will be described below in greater detail with reference to the following examples.

EXAMPLE 1

Into a flask equipped with a thermometer, stirrer, gas-introducing pipe and reflux condenser are placed 95 g (0.52 mole) of m-phenoxytoluene, 10 g of azobisisobutyronitrile, 1 g of piperidine and 1,300 g of carbon tetrachloride. The mixture is heated with stirring at a temperature of 78° to 82° C. to bring the system in a mildly reflux state. To the flask are blown 0.023 mole/min. of chlorine and the mixture is reacted for one hour. After completion of the reaction, the mixture is cooled. The carbon tetrachloride is distilled off at a reduced pressure, giving a slightly yellow product. Analysis of the product by gas chromatography shows 1.2% (yield, same in hereinafter) of m-phenoxybenzyl chloride, 95.0% of m-phenoxybenzal chloride, 2.8% of m-phenoxyphenyl trichloromethane and 1.0% of nuclear-chlorinated compounds. For comparison, the same reaction is carried out with exception that piperidine is not added. The result shows 70.8% of m-phenoxytoluene, 28.2% of m-phenoxybenzyl chloride, 0% of m-phenoxybenzal chloride and 1.0% of nuclear-chlorinated compounds.

EXAMPLES 2 TO 17

Reactions are conducted in a similar manner as in Example 1 with use of typical phenoxytoluene derivatives in Table 1. The results are also shown in Table.

TABLE 1

Chlorination of phenoxytoluenes in the coexistence of piperidine

| EX. No. | Starting material (g) | Reac. time (min.) | Products | (yield, %) |
|---|---|---|---|---|
| 2 | m-phenoxytoluene (95) | 30 | m-phenoxytoluene | (3.4) |
| | | | m-phenoxybenzyl chloride | (92.6) |
| | | | m-phenoxybenzal chloride | (3.3) |
| | | | nucleus-substituted | (0.7) |
| 3 | p-phenoxytoluene (95) | 60 | p-phenoxybenzyl chloride | (1.7) |
| | | | p-phenoxybenzal chloride | (94.0) |
| | | | p-phenoxyphenyl trichloromethane | (2.2) |
| | | | nucleus-substituted | (2.1) |
| 4 | 3-phenoxy-6-chloro-toluene (114) | 72 | 3-phenoxy-6-chloro-benzyl chloride | (7.5) |
| | | | 3-phenoxy-6-chloro-benzal chloride | (90.5) |
| | | | 3-phenoxy-6-chloro-phenyl trichloro-methane | (1.0) |
| | | | nucleus-substituted | (1.0) |
| 5 | m,m'-dimethyldi-phenyl ether (103) | 120 | m,m'-di(chloro-methyl)diphenyl ether | (2.2) |
| | | | m,m'-di(dichloro-methyl)diphenyl ether | (90.6) |
| | | | m,m'-di(trichloro-methyl)diphenyl ether | (4.7) |
| | | | nucleus-substituted | (2.5) |
| 6 | m-(m-chloromethyl-phenoxy)toluene (121) | 72 | m-(m-chloromethyl-phenoxy)toluene | (5.3) |
| | | | m-(m-dichloro-methylphenoxy) benzyl chloride | (90.3) |
| | | | m-(m-trichloro-methylphenoxy) benzal chloride | (3.4) |
| | | | nucleus-substituted | (1.0) |
| 7 | m-(p-benzoylphen-oxy)toluene (150) | 36 | m-(p-benzoylphen-oxy)toluene | (4.3) |
| | | | m-(p-benzoylphen-oxy)benzyl chloride | (91.5) |
| | | | m-(p-benzoylphen-oxy)benzal chloride | (3.2) |
| | | | nucleus-substituted | (1.0) |
| 8 | m-(p-benzoylphen-oxy)toluene (150) | 72 | m-(p-benzoylphen-oxy)benzyl chloride | (3.5) |
| | | | m-(p-benzoylphen-oxy)benzal chloride | (93.0) |
| | | | m-(p-benzoylphen-oxy)phenyl tri-chloromethane | (2.3) |
| | | | nucleus-substituted | (1.2) |
| 9 | m-(p-cyanophenoxy) | 72 | m-(p-cyanophenoxy)- | |

TABLE 1-continued

Chlorination of phenoxytoluenes in the coexistence of piperidine

| EX. No. | Starting material (g) | Reac. time (min.) | Products | (yield, %) |
|---|---|---|---|---|
| | toluene (109) | | benzyl chloride | (1.9) |
| | | | m-(p-cyanophenoxy)-benzal chloride | (91.6) |
| | | | m-(p-cyanophenoxy)-phenyl trichloro-methane | (4.8) |
| | | | nucleus-substituted | (1.7) |
| 10 | m-(p-nitrophenoxy) toluene (119) | 84 | m-(p-nitrophenoxy)-benzyl chloride | (6.8) |
| | | | m-(p-nitrophenoxy)-benzal chloride | (89.2) |
| | | | m-(p-nitrophenoxy)-phenyl trichloro-methane | (3.3) |
| | | | nucleus-substituted | (0.7) |
| 11 | m-(p-phenylphen-oxy)toluene (135) | 36 | m-(p-phenylphen-oxy)toluene | (4.2) |
| | | | m-(p-phenylphen-oxy)benzyl chloride | (92.7) |
| | | | m-(p-phenylphen-oxy)benzal chloride | (2.8) |
| | | | nucleus-substituted | (0.3) |
| 12 | m-(p-phenylphen-oxy)toluene (135) | 72 | m-(p-phenylphen-oxy)benzyl chloride | (3.1) |
| | | | m-(p-phenylphen-oxy)benzal chloride | (92.1) |
| | | | m-(p-phenylphen-oxy)phenyl trichloromethane | (3.3) |
| | | | nucleus-substituted | (1.5) |
| 13 | m-(p-benzylphen-oxy)toluene (143) | 72 | m-(p-benzylphen-oxy)benzyl chloride | (1.2) |
| | | | m-(p-benzylphen-oxy)benzal chloride | (93.7) |
| | | | m-(p-benzylphen-oxy)phenyl trichloromethane | (3.1) |
| | | | nucleus-substituted | (2.0) |
| 14 | m-(p-benzyloxy-phenoxy)toluene (151) | 72 | m-(p-benzyloxy-phenoxy)benzyl chloride | (2.7) |
| | | | m-(p-benzyloxy-phenoxy)benzal chloride | (91.6) |
| | | | m-(p-benzyloxy-phenoxy)phenyl trichloromethane | (4.0) |
| | | | nucleus-substituted | (1.7) |
| 15 | p-(m-tolyloxy) phenyl benzoate (158) | 72 | p-(m-chloromethyl-phenoxy)phenyl benzoate | (2.1) |
| | | | p-(m-dichloro-methylphenoxy)-phenyl benzoate | (92.7) |
| | | | p-(m-trichloro-methylphenoxy)-phenyl benzoate | (3.6) |
| | | | nucleus-substituted | (1.6) |
| 16 | m-(p-methoxyphen-oxy)toluene (111) | 35 | m-(p-methoxyphen-oxy)toluene | (3.2) |
| | | | m-(p-methoxyphen-oxy)benzyl chloride | (92.7) |
| | | | m-(p-methoxyphen-oxy)benzal chloride | (3.1) |
| | | | nucleus-substituted | (1.0) |
| 17 | m-(p-methoxycar-bonyl phenoxy)-toluene (126) | 35 | m-(p-methoxy-carbonyl phenoxy)-toluene | (5.4) |
| | | | m-(p-methoxy-carbonyl phenoxy)-benzyl chloride | (90.3) |
| | | | m-(p-methoxy-carbonyl phenoxy)-benzal chloride | (2.7) |
| | | | nucleus-substituted | (1.6) |

EXAMPLE 18

Chlorination reactions are conducted in a similar manner as in Example 1 with use of m-phenoxytoluene and typical nitrogen- of sulfur-containing compounds listed in Table 2. The results are also given in Table.

TABLE 2

Effect of nitrogen-containing and sulfur-containing compounds on the chlorination of m-phenoxytoluene

| No. | Nitrogen-containing or sulfur-containing compound | Reac. time (hr) | Products (Yield, %) (1) | (2) | (3) | (4) | (5) |
|---|---|---|---|---|---|---|---|
| 1 | Stearylamine | 1 | — | 1.4 | 92.6 | 2.9 | 3.1 |
| 2 | Diethanolamine | 1 | — | 1.6 | 93.7 | 2.6 | 2.1 |
| 3 | Cyclohexylamine | 1 | — | 4.1 | 92.8 | 1.2 | 1.9 |
| 4 | N,N—diethylaniline | 0.5 | 3.3 | 92.6 | 3.2 | — | 0.9 |
| 5 | N,N—diethylaniline | 1 | — | 1.0 | 95.3 | 1.9 | 1.8 |
| 6 | Quinoline | 1 | — | 2.8 | 93.4 | 2.1 | 1.7 |
| 7 | 1,8-diazabicyclo(5,4,0)-7-undecene | 1 | — | 1.6 | 95.7 | 2.0 | 0.7 |
| 8 | 1,4-diazabicyclo(2,2,2) octane | 1 | — | 1.8 | 95.6 | 1.7 | 0.9 |
| 9 | Morpholine | 0.5 | 5.4 | 90.4 | 3.1 | — | 1.1 |
| 10 | Morpholine | 1 | — | 2.9 | 92.2 | 3.5 | 1.4 |
| 11 | Di-n-dodecyl sulfide | 0.5 | 4.8 | 93.1 | 1.3 | — | 0.8 |
| 12 | Di-n-dodecyl sulfide | 1 | — | 1.2 | 96.8 | 0.8 | 1.2 |
| 13 | Diphenyl sulfide | 1 | — | 2.3 | 93.5 | 1.9 | 2.3 |
| 14 | Dicyclohexyl sulfide | 1 | — | 1.9 | 93.9 | 3.2 | 1.0 |
| 15 | 2,2'-dipyridyl sulfide | 1 | — | 1.2 | 93.1 | 2.1 | 3.6 |
| 16 | Di-tert-butyl disulfide | 1 | — | 9.1 | 87.9 | 2.2 | 0.8 |
| 17 | Diphenyl disulfide | 1 | — | 5.1 | 90.6 | 2.4 | 1.9 |
| 18 | Dicyclohexyl disulfide | 0.5 | 4.0 | 90.1 | 5.4 | — | 0.5 |
| 19 | Dicyclohexyl disulfide | 1 | — | 3.1 | 94.7 | 1.3 | 0.9 |
| 20 | 2,2'-dibenzothiazolyl disulfide | 1 | — | 2.6 | 95.1 | 1.5 | 0.8 |
| 21 | Diethyl tetrasulfide | 1 | — | 2.8 | 94.8 | 1.4 | 1.0 |
| 22 | Tetrahydrothiophene | 1 | — | 4.7 | 91.2 | 2.1 | 2.0 |
| 23 | Thiophene | 0.5 | 4.5 | 90.8 | 3.4 | — | 1.3 |
| 24 | Thiophene | 1 | — | 3.6 | 92.7 | 1.9 | 1.8 |
| 25 | 2-phenyl-1,3-dithian | 1 | — | 2.7 | 93.4 | 2.7 | 1.2 |
| 26 | n-octyl mercaptan | 1.2 | — | 4.0 | 92.8 | 2.3 | 0.9 |
| 27 | Cyclohexyl mercaptan | 0.6 | 5.1 | 90.2 | 3.6 | — | 1.1 |
| 28 | Cyclohexyl mercaptan | 1 | — | 2.9 | 91.8 | 3.6 | 1.7 |
| 29 | Thiophenol | 1 | — | 4.8 | 90.3 | 2.9 | 2.0 |
| 30 | 2-mercaptobenzothiazole | 1 | — | 8.0 | 88.5 | 2.0 | 1.5 |

(1) 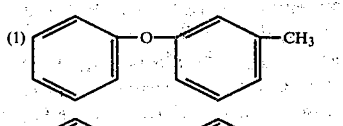

(2) 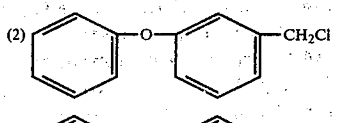

(3) 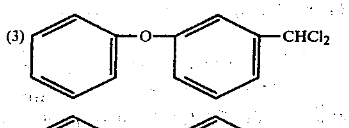

(4) 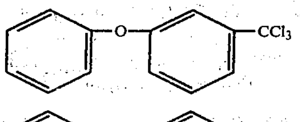

(5) 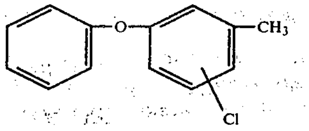

EXAMPLE 19

The procedure of Example 1 is followed with use of 95 g (0.52 mole) of m-phenoxytoluene, 10 g of azobisisobutyronitrile, 1 g of N-pentamethylenedithiocarbamic acid piperidinium salt and 1,300 g of carbon tetrachloride. The reaction time is 75 minutes. Analysis of the product by gas chromatography shows 0.9% of m-phenoxybenzyl chloride, 96.8% of m-phenoxybenzal chloride, 1.3% of m-phenoxyphenyl trichloromethane and 1.0% of nuclear-chlorinated compounds. For comparison, the same reaction is conducted, except that the above piperidium salt is not used. The result shows 41.0% of m-phenoxytoluene, 45.7% of m-phenoxybenzyl chloride, 12.1% of m-phenoxybenzal chloride and 1.2% of nuclear-chlorinated compounds.

EXAMPLE 20

Exactly the same procedure as in Example 19 is followed except that 1 g of N-diethyleneoxy-2-benzothiazolyl sulfenamide is used in place of 1 g of N-pentamethylenedithiocarbamic acid piperidinium salt. The result shows 2.1% of m-phenoxybenzyl chloride, 95.6% of m-phenoxybenzal chloride, 1.8% of m-phenoxyphenyl trichloromethane and 0.5% of nuclear-chlorinated products. The similar reaction without the above sulfenamide gives 41.0% of m-phenoxytoluene, 45.7% of m-phenoxybenzyl chloride, 12.1% of m-phenoxybenzal chloride and 1.2% of nuclear-chlorinated compounds.

EXAMPLES 21 TO 36

Table 3 shows the results of reactions which are conducted in a similar manner as in Example 19 with use of typical phenoxytoluene derivatives.

TABLE 3

Chlorination of phenoxytoluenes in the coexistence of piperidinium salt of N—pentamethylenedithiocarbamic acid

| No. | Starting material (g) | Reac. time (min.) | Products | (yield, %) |
|---|---|---|---|---|
| 21 | m-phenoxytoluene (95) | 35 | m-phenoxytoluene | (2.8) |
| | | | m-phenoxybenzyl chloride | (93.4) |
| | | | m-phenoxybenzal chloride | (2.9) |
| | | | nucleus-substituted | (0.9) |
| 22 | p-phenoxytoluene (95) | 75 | p-phenoxybenzyl chloride | (2.0) |
| | | | p-phenoxybenzal chloride | (94.5) |
| | | | p-phenoxyphenyl trichloromethane | (2.0) |
| | | | nucleus-substituted | (1.5) |
| 23 | 3-phenoxy-6-chloro-toluene (114) | 85 | 3-phenoxy-6-chloro-benzyl chloride | (5.6) |
| | | | 3-phenoxy-6-chloro-benzal chloride | (91.3) |
| | | | 3-phenoxy-6-chloro-phenyl trichloro-methane | (2.1) |
| | | | nucleus-substituted | (1.0) |
| 24 | m,m'-dimethyldi-phenyl ether (103) | 150 | m,m'-di(chloro-methyl)diphenyl ether | (2.5) |
| | | | m,m'-di(dichloro-methyl)diphenyl ether | (89.8) |
| | | | m,m'-di(trichloro-methyl)diphenyl ether | (4.8) |
| | | | nucleus-substituted | (2.9) |
| 25 | m-(m-chloromethyl-phenoxy)toluene (121) | 85 | m-(m-chloromethyl-phenoxy)toluene | (3.2) |
| | | | m-(m-dichloro-methylphenoxy) benzyl chloride | (91.0) |
| | | | m-(m-trichloro-methylphenoxy) benzal chloride | (3.7) |
| | | | nucleus-substituted | (2.1) |

TABLE 3-continued

Chlorination of phenoxytoluenes in the coexistence of piperidinium salt of N—pentamethylenedithiocarbamic acid

| No. | Starting material (g) | Reac. time (min.) | Products | (yield, %) |
|---|---|---|---|---|
| 26 | m-(p-benzoylphen-oxy)toluene (150) | 40 | m-(p-benzoylphen-oxy)toluene | (3.9) |
| | | | m-(p-benzoylphen-oxy)benzyl chloride | (90.8) |
| | | | m-(p-benzoylphen-oxy)benzal chloride | (4.2) |
| | | | nucleus-substituted | (1.1) |
| 27 | m-(p-benzoylphen-oxy)toluene (150) | 80 | m-(p-benzoylphen-oxy)benzyl chloride | (2.8) |
| | | | m-(p-benzoylphen-oxy)benzal chloride | (93.7) |
| | | | m-(p-benzoylphen-oxy)phenyl tri-chloromethane | (2.0) |
| | | | nucleus-substituted | (1.5) |
| 28 | m-(p-cyanophenoxy) toluene (109) | 85 | m-(p-cyanophenoxy)-benzyl chloride | (1.2) |
| | | | m-(p-cyanophenoxy)-benzal chloride | (92.1) |
| | | | m-(p-cyanophenoxy)-phenyl trichloro-methane | (4.3) |
| | | | nucleus-substituted | (2.4) |
| 29 | m-(p-nitrophenoxy) toluene (119) | 85 | m-(p-nitrophenoxy)-benzyl chloride | (5.9) |
| | | | m-(p-nitrophenoxy)-benzal chloride | (90.2) |
| | | | m-(p-nitrophenoxy)-phenyl trichloro-methane | (2.4) |
| | | | nucleus-substituted | (1.5) |
| 30 | m-(p-phenylphen-oxy)toluene (135) | 40 | m-(p-phenylphen-oxy)toluene | (3.7) |
| | | | m-(p-phenylphen-oxy)benzyl chloride | (91.0) |
| | | | m-(p-phenylphen-oxy)benzal chloride | (4.1) |
| | | | nucleus-substituted | (1.2) |
| 31 | m-(p-phenylphen-oxy)toluene (135) | 80 | m-(p-phenylphen-oxy)benzyl chloride | (3.9) |
| | | | m-(p-phenylphen-oxy)benzal chloride | (92.5) |
| | | | m-(p-phenylphen-oxy)phenyl trichloro-methane | (2.0) |
| | | | nucleus-substituted | (1.6) |
| 32 | m-(p-benzylphen-oxy)toluene (143) | 80 | m-(p-benzylphen-oxy)benzyl chloride | (2.5) |
| | | | m-(p-benzylphen-oxy)benzal chloride | (93.6) |
| | | | m-(p-benzylphen-oxy)phenyl trichloro-methane | (1.8) |
| | | | nucleus-substituted | (2.1) |
| 33 | m-(p-benzyloxy-phenoxy)toluene (151) | 80 | m-(p-benzyloxy-phenoxy)benzyl chloride | (2.2) |
| | | | m-(p-benzyloxy-phenoxy)benzal chloride | (93.3) |
| | | | m-(p-benzyloxy-phenoxy)phenyl trichloromethane | (2.7) |
| | | | nucleus-substituted | (1.8) |
| 34 | p-(m-tolyloxy) phenyl benzoate (158) | 80 | p-(m-chloromethyl-phenoxy)phenyl benzoate | (1.8) |
| | | | p-(m-dichloro-methylphenoxy)-phenyl benzoate | (94.5) |
| | | | p-(m-trichloro-methylphenoxy)-phenyl benzoate | (2.6) |
| | | | nucleus-substituted | (1.1) |
| 35 | m-(p-methoxyphen- | 35 | m-(p-methoxyphen- | |

TABLE 3-continued

Chlorination of phenoxytoluenes in the coexistence of piperidinium salt of N—pentamethylenedithiocarbamic acid

| No. | Starting material (g) | Reac. time (min.) | Products | (yield, %) |
|---|---|---|---|---|
| | oxy)toluene (111) | | oxy)toluene | (3.9) |
| | | | m-(p-methoxyphenoxy)benzyl chloride | (90.5) |
| | | | m-(p-methoxyphenoxy)benzal chloride | (3.5) |
| | | | nucleus-substituted | (2.1) |
| 36 | m-(p-methoxycarbonyl phenoxy)-toluene (126) | 35 | m-(p-methoxycarbonyl phenoxy)toluene | (3.6) |
| | | | m-(p-methoxycarbonyl phenoxy)benzyl chloride | (89.5) |
| | | | m-(p-methoxycarbonyl phenoxy)benzal chloride | (4.4) |
| | | | nucleus-substituted | (2.5) |

EXAMPLES 37 TO 52

Table 4 shows the results of reactions which are conducted in a similar manner as in Example 20 with use of typical phenoxytoluene derivatives.

TABLE 4

Chlorination of phenoxytoluenes in the coexistence of N—diethyleneoxy-2-benzothiazolyl sulfenamide

| EX. No. | Starting material (g) | Reac. time (min.) | Products | (yield, %) |
|---|---|---|---|---|
| 37 | m-phenoxytoluene (95) | 37 | m-phenoxytoluene | (4.1) |
| | | | m-phenoxybenzyl chloride | (94.0) |
| | | | m-phenoxybenzal chloride | (1.5) |
| | | | nucleus-substituted | (0.4) |
| 38 | p-phenoxytoluene (95) | 76 | p-phenoxybenzyl chloride | (4.2) |
| | | | p-phenoxybenzal chloride | (93.2) |
| | | | p-phenoxyphenyl trichloromethane | (1.8) |
| | | | nucleus-substituted | (0.8) |
| 39 | 3-phenoxy-6-chlorotoluene (114) | 88 | 3-phenoxy-6-chlorobenzyl chloride | (4.7) |
| | | | 3-phenoxy-6-chlorobenzal chloride | (92.8) |
| | | | 3-phenoxy-6-chlorophenyl trichloromethane | (1.8) |
| | | | nucleus-substituted | (0.7) |
| 40 | m,m'-dimethyldiphenyl ether (103) | 150 | m,m'-di(chloromethyl)diphenyl ether | (7.2) |
| | | | m,m'-di(dichloromethyl)diphenyl ether | (88.7) |
| | | | m,m'-di(trichloromethyl)diphenyl ether | (3.0) |
| | | | nucleus-substituted | (1.1) |
| 41 | m-(m-chloromethylphenoxy)toluene (121) | 86 | m-(m-chloromethylphenoxy)toluene | (3.7) |
| | | | m-(m-dichloromethylphenoxy) benzyl chloride | (92.4) |
| | | | m-(m-trichloromethylphenoxy) benzal chloride | (3.1) |
| | | | nucleus-substituted | (0.8) |
| 42 | m-(p-benzoylphenoxy)toluene (150) | 44 | m-(p-benzoylphenoxy)toluene | (5.7) |
| | | | m-(p-benzoylphenoxy)benzyl chloride | (91.6) |

TABLE 4-continued

Chlorination of phenoxytoluenes in the coexistence of N—diethyleneoxy-2-benzothiazolyl sulfenamide

| EX. No. | Starting material (g) | Reac. time (min.) | Products | (yield, %) |
|---|---|---|---|---|
| | | | m-(p-benzoylphenoxy)benzal chloride | (2.2) |
| | | | nucleus-substituted | (0.5) |
| 43 | m-(p-benzoylphenoxy)toluene (150) | 80 | m-(p-benzoylphenoxy)benzyl chloride | (3.0) |
| | | | m-(p-benzoylphenoxy)benzal chloride | (94.9) |
| | | | m-(p-benzoylphenoxy)phenyl trichloromethane | (1.3) |
| | | | nucleus-substituted | (0.8) |
| 44 | m-(p-cyanophenoxy) toluene (109) | 87 | m-(p-cyanophenoxy)-benzyl chloride | (4.3) |
| | | | m-(p-cyanophenoxy)-benzal chloride | (92.0) |
| | | | m-(p-cyanophenoxy)-phenyl trichloromethane | (2.5) |
| | | | nucleus-substituted | (1.2) |
| 45 | m-(p-nitrophenoxy) toluene (119) | 90 | m-(p-nitrophenoxy)-benzyl chloride | (8.5) |
| | | | m-(p-nitrophenoxy)-benzal chloride | (88.1) |
| | | | m-(p-nitrophenoxy)-phenyl trichloromethane | (2.0) |
| | | | nucleus-substituted | (1.4) |
| 46 | m-(p-phenylphenoxy)toluene (135) | 42 | m-(p-phenylphenoxy)toluene | (3.5) |
| | | | m-(p-phenylphenoxy)benzyl chloride | (93.7) |
| | | | m-(p-phenylphenoxy)benzal chloride | (2.0) |
| | | | nucleus-substituted | (0.8) |
| 47 | m-(p-phenylphenoxy)toluene (135) | 84 | m-(p-phenylphenoxy)benzyl chloride | (1.1) |
| | | | m-(p-phenylphenoxy)benzal chloride | (95.8) |
| | | | m-(p-phenylphenoxy)phenyl trichloromethane | (2.0) |
| | | | nucleus-substituted | (1.1) |
| 48 | m-(p-benzylphenoxy)toluene (143) | 85 | m-(p-benzylphenoxy)benzyl chloride | (2.7) |
| | | | m-(p-benzylphenoxy)benzal chloride | (94.9) |
| | | | m-(p-benzylphenoxy)phenyl trichloromethane | (1.5) |
| | | | nucleus-substituted | (0.9) |
| 49 | m-(p-benzyloxyphenoxy)toluene (151) | 82 | m-(p-benzyloxyphenoxy)benzyl chloride | (3.5) |
| | | | m-(p-benzyloxyphenoxy)benzal chloride | (94.0) |
| | | | m-(p-benzyloxyphenoxy)phenyl trichloromethane | (1.8) |
| | | | nucleus-substituted | (0.7) |
| 50 | p-(m-tolyloxy) phenyl benzoate (158) | 85 | p-(m-chloromethylphenoxy)phenyl benzoate | (2.0) |
| | | | p-(m-dichloromethylphenoxy)-phenyl benzoate | (95.6) |
| | | | p-(m-trichloromethylphenoxy)-phenyl benzoate | (1.9) |
| | | | nucleus-substituted | (0.5) |
| 51 | m-(p-methoxyphenoxy)toluene (111) | 40 | m-(p-methoxyphenoxy)toluene | (3.6) |
| | | | m-(p-methoxyphenoxy)benzyl chloride | (91.0) |
| | | | m-(p-methoxyphenoxy)benzal chloride | (4.1) |

TABLE 4-continued

| Chlorination of phenoxytoluenes in the coexistence of N—diethyleneoxy-2-benzothiazolyl sulfenamide | | | | |
|---|---|---|---|---|
| EX. No. | Starting material (g) | Reac. time (min.) | Products | (yield, %) |
| | | | nucleus-substituted | (1.3) |
| 52 | m-(p-methoxycarbonyl phenoxy)-toluene (126) | 40 | m-(p-methoxycarbonyl phenoxy)toluene | (4.8) |
| | | | m-(p-methoxycarbonyl phenoxy)benzyl chloride | (90.4) |
| | | | m-(p-methoxycarbonyl phenoxy)benzal chloride | (3.2) |
| | | | nucleus-substituted | (1.6) |

EXAMPLE 53

Table 5 shows the results of reactions which are conducted in a similar manner as in Example 19 with use of m-phenoxytoluene and typical sulfur-containing compounds.

TABLE 5

| Effect of sulfur-containing compounds on the chlorination of m-phenoxytoluene | | | | | | | |
|---|---|---|---|---|---|---|---|
| | | Reac. time | Products (Yield, %) | | | | |
| No. | Sulfur-containing compound | (min.) | (1) | (2) | (3) | (4) | (5) |
| 1 | Methyl cyclohexyl thioketone | 70 | — | 6.7 | 89.0 | 3.1 | 1.2 |
| 2 | 4,4'-Bis(N,N—dimethyl-amino)thiobenzophenone | 70 | — | 3.5 | 90.8 | 3.9 | 1.8 |
| 3 | 1-Isopropyl-3-(n-dodecyl)-2-thiourea | 35 | 3.8 | 90.8 | 4.4 | — | 1.0 |
| 4 | 1-Isopropyl-3-(n-dodecyl)-2-thiourea | 75 | — | 2.4 | 93.5 | 2.8 | 1.3 |
| 5 | 1-(p-Tolyl)-3-(2-pyridyl)-2-thiourea | 75 | — | 3.4 | 93.8 | 1.6 | 1.2 |
| 6 | 1,1,3,3-Tetra-n-propyl-2-thiourea | 75 | — | 3.9 | 91.7 | 3.4 | 1.0 |
| 7 | 1,4-Diethyl-1,4-diphenyl-3-thiosemicarbazide | 75 | — | 4.1 | 92.1 | 2.7 | 1.1 |
| 8 | 1-Isonicotinoyl-4-(n-octadecanoyl)-3-thiosemicarbazide | 75 | — | 3.3 | 93.4 | 2.0 | 1.3 |
| 9 | 1-(n-Heptadecyl)-4-thiosemicarbazone | 75 | — | 3.8 | 92.2 | 3.1 | 0.9 |
| 10 | 1-Pentamethylene-4-thiosemicarbazone | 35 | 3.9 | 90.3 | 4.6 | — | 1.2 |
| 11 | 1-Pentamethylene-4-thiosemicarbazone | 75 | — | 2.4 | 93.7 | 2.4 | 1.5 |
| 12 | 1,5-Diphenyl-3-thiocarbohydrazide | 75 | — | 3.1 | 92.9 | 2.1 | 1.9 |
| 13 | Dithizone | 75 | — | 4.6 | 91.9 | 1.7 | 1.8 |
| 14 | 1,7-Di-n-heptadecyl-4-bisthiocarbohydrazone | 75 | — | 4.0 | 92.4 | 2.5 | 1.1 |
| 15 | 1,7-Dipentamethylene-4-bisthiocarbohydrazone | 75 | — | 2.6 | 93.5 | 2.9 | 1.0 |
| 16 | 5-Ethyl-2-thiobiuret | 73 | — | 4.0 | 90.4 | 3.5 | 2.1 |
| 17 | 5-(n-Propyl)-2,4-dithiobiuret | 75 | — | 2.8 | 92.3 | 3.0 | 1.9 |
| 18 | N,N',N'',N'''—Hexamethylguanyl thiourea | 70 | — | 5.0 | 89.0 | 3.9 | 2.1 |
| 19 | n-Heptadecylthioamide | 75 | — | 5.8 | 90.1 | 2.8 | 1.3 |
| 20 | N—Cyclohexylthiobenzamide | 75 | — | 4.8 | 90.9 | 3.1 | 1.2 |
| 21 | 2-Benzothiazolylethyl thioanilide | 75 | — | 5.0 | 91.7 | 2.2 | 1.1 |
| 22 | Thiophenylacetohydrazide | 80 | — | 5.1 | 88.7 | 2.9 | 3.3 |
| 23 | 2,4-Dichlorophenyl thiophenylacetohydrazone | 75 | — | 4.3 | 90.3 | 2.4 | 3.0 |
| 24 | N—(n-Octyl)-N—aminoethyl dithiocarbamic acid | 75 | — | 4.1 | 93.4 | 1.3 | 1.2 |
| 25 | 2-Thiazolyldithiocarbamic acid triethylammonium salt | 34 | 1.2 | 94.0 | 3.8 | — | 1.0 |
| 26 | 2-Thiazolyldithiocarbamic acid triethylammonium salt | 75 | — | 1.3 | 95.6 | 2.0 | 1.1 |
| 27 | Cyclohexyldithiocarbamic acid cyclohexylammonium salt | 74 | — | 4.4 | 90.8 | 3.1 | 1.7 |
| 28 | N,N—Dimethyl S—(n-hexadecyl)dithiocarbamate | 75 | — | 3.3 | 91.8 | 2.9 | 2.0 |
| 29 | N,N—Dimethyl S—(2-benzothiazolyl)dithiocarbamate | 35 | 2.6 | 93.6 | 2.9 | — | 0.9 |
| 30 | N,N—Dimethyl S—(2-benzothiazolyl)dithiocarbamate | 75 | — | 2.1 | 94.4 | 1.4 | 2.1 |
| 31 | N—Pentamethylene S— | 80 | — | 5.1 | 92.7 | 1.0 | 1.2 |

TABLE 5-continued

Effect of sulfur-containing compounds on the chlorination of m-phenoxytoluene

| No. | Sulfur-containing compound | Reac. time (min.) | Products (Yield, %) (1) | (2) | (3) | (4) | (5) |
|---|---|---|---|---|---|---|---|
| | mercaptoethyl dithiocarbamate | | | | | | |
| 32 | N—Diethyleneoxy S—hydroxyethyl dithiocarbamate | 77 | — | 5.7 | 91.8 | 1.2 | 1.3 |
| 33 | N—Carboxymethyl O—(η-hexadecyl) thioncarbamate | 75 | — | 7.1 | 90.0 | 1.8 | 1.1 |
| 34 | N—Pentamethylene O—(n-propyl) thioncarbamate | 75 | — | 6.6 | 89.1 | 3.1 | 1.2 |
| 35 | Diethyl dithiocarbamyl sulfenamide | 78 | — | 3.8 | 92.4 | 2.1 | 1.7 |
| 36 | Benzyl thionpropionate | 75 | — | 4.1 | 88.7 | 4.1 | 3.1 |
| 37 | Isoamyl p-thiontoluate | 75 | — | 6.1 | 87.9 | 3.8 | 2.2 |
| 38 | Dithiobenzoic acid | 85 | — | 2.0 | 90.2 | 4.7 | 3.1 |
| 39 | Ethyl dithio-n-heptanoate | 76 | — | 3.4 | 90.1 | 3.7 | 2.8 |
| 40 | n-Buthyl dithiocyclohexanecarboxylate | 75 | — | 3.5 | 90.0 | 4.0 | 2.5 |
| 41 | n-Dodecyl phenylthioncarbonate | 75 | — | 7.4 | 89.3 | 2.1 | 1.2 |
| 42 | Tetramethylenethioncarbonate | 75 | — | 3.9 | 92.1 | 3.0 | 1.0 |
| 43 | Di-n-octadecyl trithiocarbonate | 78 | — | 4.9 | 91.8 | 1.9 | 1.4 |
| 44 | Di-n-dodecyl trithiocarbonate | 76 | — | 5.6 | 90.2 | 2.2 | 2.0 |
| 45 | Dicyclohexyl trithiocarbonate | 76 | — | 5.4 | 90.7 | 2.0 | 1.9 |
| 46 | S,O—(di-n-dodecyl)-xanthate | 75 | — | 4.1 | 91.2 | 3.4 | 1.3 |
| 47 | S—carboxydecamethylene O—(n-dodecyl)xanthate | 75 | — | 5.3 | 90.9 | 2.8 | 1.0 |
| 48 | S—(n-hexadecyl) O—cyclohexyl xanthate | 75 | — | 5.4 | 90.3 | 3.1 | 1.2 |
| 49 | 1-(n-dodecylidene) O—ethylthioncarbazate | 75 | — | 5.0 | 91.9 | 1.9 | 1.2 |
| 50 | 1-(n-dodecylidene) S—ethyldithiocarbazate | 75 | — | 3.1 | 93.4 | 2.2 | 1.3 |
| 51 | Cyclohexyl isothiocyanate | 75 | — | 6.3 | 88.1 | 3.9 | 1.7 |
| 52 | p-(N,N—dimethylamino)-phenyl isothiocyanate | 76 | — | 5.2 | 90.0 | 3.0 | 1.8 |
| 53 | 6-Isothiocyanoquinoline | 75 | — | 3.9 | 90.8 | 3.2 | 2.1 |
| 54 | Hexamethylene diisothiocyanate | 35 | 5.1 | 88.9 | 5.0 | — | 1.0 |
| 55 | Hexamethylene diisothiocyanate | 75 | — | 6.4 | 89.0 | 3.5 | 1.1 |
| 56 | Methylenebistetramethylene thiourea | 75 | — | 5.4 | 91.3 | 2.1 | 1.2 |
| 57 | Bis(N—trimethylenethioacetamide) | 75 | — | 4.1 | 90.8 | 3.1 | 2.0 |
| 58 | Ethylenebisdithiocarbamic acid diammonium salt | 80 | — | 1.7 | 96.0 | 1.2 | 1.1 |
| 59 | O,O'—dicyclohexyl S,S'—methylenebisxanthate | 77 | — | 4.3 | 92.4 | 2.3 | 1.0 |
| 60 | Cyclohexylxanthogenemonosulfide | 75 | — | 3.8 | 92.9 | 2.1 | 1.2 |
| 61 | n-Hexadecyl dixanthogene | 76 | — | 2.7 | 93.4 | 2.8 | 1.1 |
| 62 | Benzyl dixanthogene | 75 | — | 2.2 | 94.1 | 2.7 | 1.0 |
| 63 | Ethyl dixanthogene disulfide | 78 | — | 1.5 | 95.6 | 1.8 | 1.1 |
| 64 | N,N'—dimorpholino dithiooxalic diamide | 80 | — | 2.6 | 90.9 | 4.1 | 2.4 |
| 65 | Bis(piperidinothiocarbonyl) monosulfide | 75 | — | 4.0 | 91.7 | 2.3 | 2.0 |
| 66 | Bis(morpholinothiocarbonyl) monosulfide | 75 | — | 3.1 | 92.9 | 2.1 | 1.9 |
| 67 | Bis(piperidinothiocarbonyl) disulfide | 75 | — | 2.3 | 93.8 | 2.0 | 1.9 |
| 68 | Bis(morpholinothiocarbonyl) disulfide | 75 | — | 2.1 | 94.1 | 2.0 | 1.8 |
| 69 | Ethylene-1,2-bis[1,2-(dithiocarbamoyl)-ethylene] disulfide | 78 | — | 1.9 | 92.7 | 3.4 | 2.0 |
| 70 | Bis(piperidinothiocarbonyl) hexasulfide | 80 | — | 1.2 | 94.8 | 1.9 | 2.1 |
| 71 | Pentamethylene dithiocyanate | 75 | — | 7.4 | 89.5 | 1.2 | 1.9 |
| 72 | 3-Thiocyanopyridine | 38 | 2.8 | 87.5 | 8.3 | — | 1.4 |

TABLE 5-continued

Effect of sulfur-containing compounds on the chlorination of m-phenoxytoluene

| No. | Sulfur-containing compound | Reac. time (min.) | Products (Yield, %) (1) | (2) | (3) | (4) | (5) |
|---|---|---|---|---|---|---|---|
| 73 | 3-Thiocyanopyridine | 75 | — | 5.7 | 90.2 | 1.3 | 2.8 |
| 74 | N—(n-Heptadecyl)-n-octyl sulfenamide | 75 | — | 3.4 | 93.5 | 2.4 | 0.7 |
| 75 | Tert-Butylethyl thiosulfinate | 75 | — | 5.0 | 90.2 | 2.3 | 2.5 |
| 76 | Thiostearic acid | 80 | — | 4.2 | 91.7 | 1.0 | 3.1 |
| 77 | Dicyclohexyldithiol sebacate | 75 | — | 5.0 | 91.1 | 2.2 | 1.7 |
| 78 | S,S'—Dimethylenecarboxy O,O'—diethylbisthiol carbonate | 75 | — | 11.3 | 86.4 | 1.1 | 1.2 |
| 79 | Diisoamyldithiol carbonate | 75 | — | 7.2 | 89.5 | 1.7 | 1.6 |
| 80 | N—(ζ-Aminohexamethyl) thiocarbamic acid | 80 | — | 4.3 | 91.8 | 1.1 | 2.8 |
| 81 | N—Stearylthiocarbamic acid stearylammonium salt | 35 | 4.5 | 92.5 | 1.9 | — | 1.1 |
| 82 | N—Stearylthiocarbamic acid stearylammonium salt | 75 | — | 1.1 | 95.1 | 1.8 | 2.0 |
| 83 | N—Pentamethylene S—phenyl thiol carbamate | 75 | — | 1.8 | 94.5 | 1.9 | 1.8 |
| 84 | 2-Thienylmercapto-acetic acid | 80 | — | 4.7 | 90.3 | 2.6 | 2.4 |
| 85 | n-Octadecylmercapto-succinic acid diethyl ester | 75 | — | 8.1 | 89.8 | 1.0 | 1.1 |
| 86 | Methylmercaptopelargonic acid amide | 80 | — | 2.6 | 92.7 | 1.9 | 2.8 |
| 87 | S,S'—Di(n-octadecyl)methyl thioacetal | 75 | — | 10.9 | 85.4 | 1.6 | 2.1 |
| 88 | S,S'—Dibenzylcyclohexyl ketone thioacetal | 76 | — | 8.5 | 88.4 | 1.9 | 1.2 |
| 89 | Tri-n-dodecyl trithio-orthoformate | 75 | — | 8.0 | 87.2 | 2.1 | 2.7 |
| 90 | Tetracyclohexyl tetra-thioorthocarbonate | 75 | — | 6.5 | 89.0 | 2.4 | 2.1 |
| 91 | 1,10-Decamethylenebis-chloroethyl sulfide | 73 | — | 5.2 | 91.2 | 1.0 | 2.6 |
| 92 | Di(N—pentamethyleneamino-ethyl) sulfide | 35 | 3.9 | 92.6 | 2.6 | — | 0.9 |
| 93 | Di(N—pentamethyleneamino-ethyl) sulfide | 75 | — | 3.5 | 93.4 | 1.1 | 2.0 |
| 94 | p-Benzylmercapto-benzaldehyde | 75 | — | 7.7 | 89.0 | 1.1 | 2.2 |
| 95 | n-Dodecylmercaptomethyl phenyl ketone | 75 | — | 7.0 | 89.7 | 1.6 | 1.7 |
| 96 | n-Octadecylmercapto-propionitrile | 78 | — | 9.7 | 86.3 | 2.2 | 1.8 |
| 97 | Dibenzoyl sulfide | 75 | — | 5.6 | 90.0 | 2.1 | 2.3 |
| 98 | Bis{2-[2-(2-chloroethyl-thio)ethylthio]ethyl} sulfide | 83 | — | 3.8 | 93.4 | 1.7 | 1.1 |
| 99 | Poly(ethylenesulfide) Mn = 1,100 | 75 | — | 4.1 | 92.6 | 2.3 | 1.0 |
| 100 | Di(κ-carboxydecyl)disulfide | 76 | — | 4.6 | 91.2 | 3.1 | 1.1 |
| 101 | Di(cyclohexyloxycarbonyl-ethyl)disulfide | 75 | — | 4.9 | 91.7 | 2.1 | 1.3 |
| 102 | Di(N—methylanilinocarbonyl-methyl)disulfide | 35 | 4.1 | 90.3 | 4.5 | — | 1.1 |
| 103 | Di(N—methylanilinocarbonyl-methyl)disulfide | 75 | — | 2.8 | 94.0 | 1.3 | 1.9 |
| 104 | Di(2,4-dichlorophenyl) disulfide | 75 | — | 5.0 | 92.0 | 1.9 | 1.1 |
| 105 | Di(N,N—dimethylamino-hexamethyl)disulfide | 80 | — | 4.2 | 92.3 | 2.1 | 1.4 |
| 106 | Di(o-formylmethylthio-phenyl)disulfide | 78 | — | 5.7 | 90.6 | 1.6 | 2.1 |
| 107 | Di(methylcarbonyl-isobutyl)disulfide | 75 | — | 6.5 | 90.3 | 2.0 | 1.2 |
| 108 | ζ-Cyano-ζ'-hydroxy dihexamethyl disulfide | 78 | — | 8.1 | 87.3 | 2.9 | 1.7 |
| 109 | Di-3-nicotinoyl disulfide | 38 | 9.2 | 87.1 | 2.4 | — | 1.3 |
| 110 | Di-3-nicotinoyl disulfide | 78 | — | 8.3 | 88.5 | 2.1 | 1.1 |
| 111 | Poly(ethylformal disulfide) | 75 | — | 4.5 | 92.1 | 1.3 | 2.1 |

TABLE 5-continued

Effect of sulfur-containing compounds on the chlorination of m-phenoxytoluene

| No. | Sulfur-containing compound | Reac. time (min.) | Products (Yield, %) (1) | (2) | (3) | (4) | (5) |
|---|---|---|---|---|---|---|---|
| | $\overline{Mn}$ = 2,400 | | | | | | |
| 112 | Poly(ethylene disulfide) $\overline{Mn}$ = 500 | 75 | — | 3.1 | 93.8 | 1.1 | 2.0 |
| 113 | Di(γ-hydroxypropyl) disulfide | 76 | — | 5.7 | 90.2 | 2.7 | 1.4 |
| 114 | Di(2-ethoxy-1-naphthyl) disulfide | 77 | — | 4.5 | 90.7 | 2.2 | 2.6 |
| 115 | Di(carboxymethyl) trisulfide | 78 | — | 5.1 | 90.5 | 1.7 | 2.7 |
| 116 | Di(p-ethoxycarbonyl-phenyl)trisulfide | 75 | — | 5.4 | 91.5 | 1.8 | 1.3 |
| 117 | Di(o-n-butylcarbamoyl-phenyl)tetrasulfide | 78 | — | 4.7 | 92.3 | 1.2 | 1.8 |
| 118 | Di(β-chloroethyl) pentasulfide | 35 | 6.4 | 90.1 | 2.1 | — | 1.4 |
| 119 | Di(β-chloroethyl) pentasulfide | 75 | — | 2.9 | 92.7 | 1.6 | 2.8 |
| 120 | Di(ethylenediamino-ethyl)tetrasulfide | 78 | — | 5.5 | 90.3 | 1.9 | 2.3 |
| 121 | Di(β-formylethyl) trisulfide | 76 | — | 6.6 | 89.8 | 1.7 | 1.9 |
| 122 | Di(acetylmethyl) trisulfide | 75 | — | 7.7 | 88.1 | 2.2 | 2.0 |
| 123 | Di(β-cyanoethyl) trisulfide | 75 | — | 9.1 | 87.9 | 1.8 | 1.2 |
| 124 | Dibenzoyl tetrasulfide | 36 | 6.5 | 88.2 | 3.4 | — | 1.9 |
| 125 | Dibenzoyl tetrasulfide | 75 | — | 5.4 | 90.3 | 1.8 | 2.5 |
| 126 | Poly(ethyl ether tetra-sulfide) $\overline{Mn}$ = 1,100 | 75 | — | 2.6 | 93.4 | 1.1 | 2.9 |
| 127 | Di(2-hydroxy-1-naphthyl) trisulfide | 80 | — | 7.5 | 87.1 | 4.3 | 1.1 |
| 128 | Di(2-ethoxy-1-naphthyl) trisulfide | 75 | — | 6.2 | 88.7 | 2.1 | 3.0 |
| 129 | κ-Mercaptoundecylic acid | 85 | — | 4.8 | 91.2 | 1.7 | 2.3 |
| 130 | Mercaptosuccinic acid ethyl ester | 84 | — | 3.8 | 92.3 | 1.6 | 2.3 |
| 131 | ε-Mercaptocaproic acid amide | 90 | — | 3.4 | 90.7 | 2.8 | 3.1 |
| 132 | Pentachlorothiophenol | 78 | — | 3.9 | 90.8 | 2.8 | 2.5 |
| 133 | N,N'—Di(γ-mercaptoiso-butyl)piperazine | 88 | — | 2.7 | 93.4 | 1.1 | 2.8 |
| 134 | β-Formylethyl mercaptan | 85 | — | 4.1 | 90.9 | 2.6 | 2.4 |
| 135 | Di(p-mercaptophenyl) ketone | 90 | — | 3.9 | 92.3 | 1.5 | 2.3 |
| 136 | β-Cyanoethyl mercaptan | 80 | — | 3.2 | 89.8 | 3.4 | 3.6 |
| 137 | Bis(ethylenedimercapto-methyl) methane | 90 | — | 3.3 | 92.7 | 1.6 | 2.4 |
| 138 | Di(β-mercaptoethyl) disulfide | 83 | — | 3.5 | 91.4 | 2.4 | 2.7 |
| 139 | Di(β-mercaptoethyl) tetrasulfide | 85 | — | 3.6 | 93.2 | 1.2 | 2.0 |

TABLE 5-continued

Effect of sulfur-containing compounds on the chlorination of m-phenoxytoluene

| No. | Sulfur-containing compound | Reac. time (min.) | Products (Yield, %) (1) | (2) | (3) | (4) | (5) |
|---|---|---|---|---|---|---|---|
| 140 | 1,6-Hexamethylene dithiol | 85 | — | 4.1 | 92.3 | 1.9 | 1.7 |

(1) 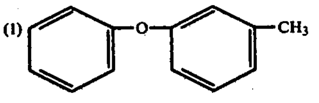

(2) 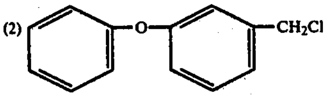

(3) 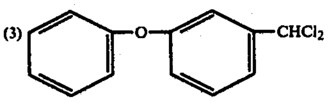

(4) 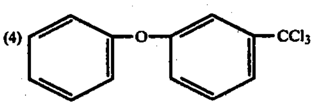

(5) 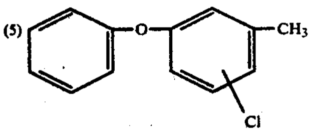

EXAMPLE 54

The procedure of Example 1 is followed with use of 95 g (0.52 mole) of m-phenoxytoluene, 10 g of azobisisobutyronitrile, 1 g of triphenylphosphine and 1,300 g of carbon tetrachloride. The reaction time is 75 minutes. Analysis of the product by gas chromatography shows 4.9% of m-phenoxybenzyl chloride, 90.1% of m-phenoxybenzal chloride, 4.2% of m-phenoxyphenyl trichloromethane and 0.8% of nuclear-chlorinated compounds. For comparison, the same reaction is conducted, except that the above triphenylphosphine is not used. The result shows 41.0% of m-phenoxytoluene, 45.7% of m-phenoxbenzyl chloride, 12.1% of m-phenoxybenzal chloride and 1.2% of nuclear-chlorinated compounds.

EXAMPLES 55 TO 70

Chlorination reactions are carried out in a similar manner as in Example 54 with use of typical phenoxytoluene derivatives listed in Table 6. The results are also given in Table.

TABLE 6

Chlorination of phenoxytoluenes in the coexistence of triphenylphosphine

| No. | Starting material (g) | Reac. time (min.) | Products | (yield, %) |
|---|---|---|---|---|
| 55 | m-phenoxytoluene (95) | 40 | m-phenoxytoluene | (4.4) |
| | | | m-phenoxybenzyl chloride | (90.3) |
| | | | m-phenoxybenzal chloride | (4.8) |
| | | | nucleus-substituted | (0.5) |
| 56 | p-phenoxytoluene (95) | 80 | p-phenoxybenzyl chloride | (4.2) |
| | | | p-phenoxybenzal chloride | (91.5) |
| | | | p-phenoxyphenyl trichloromethane | (3.4) |

TABLE 6-continued

Chlorination of phenoxytoluenes in the coexistence of triphenylphosphine

| No. | Starting material (g) | Reac. time (min.) | Products | (yield, %) |
|---|---|---|---|---|
| | | | nucleus-substituted | (0.9) |
| 57 | 3-phenoxy-6-chloro-toluene (114) | 90 | 3-phenoxy-6-chloro-benzyl chloride | (8.9) |
| | | | 3-phenoxy-6-chloro-benzal chloride | (87.6) |
| | | | 3-phenoxy-6-chloro-phenyl trichloro-methane | (2.5) |
| | | | nucleus-substituted | (1.0) |
| 58 | m,m'-dimethyldi-phenyl ether (103) | 160 | m,m'-di(chloro-methyl)diphenyl ether | (11.7) |
| | | | m,m'-di(dichloro-methyl)diphenyl ether | (80.9) |
| | | | m,m'-di(trichloro-methyl)diphenyl ether | (4.9) |
| | | | nucleus-substituted | (2.5) |
| 59 | m-(m-chloromethyl-phenoxy)toluene (121) | 90 | m-(m-chloromethyl-phenoxy)toluene | (12.6) |
| | | | m-(m-dichloro-methylphenoxy) benzyl chloride | (82.3) |
| | | | m-(m-trichloro-methylphenoxy) benzal chloride | (3.1) |
| | | | nucleus-substituted | (2.0) |
| 60 | m-(p-benzoylphen-oxy)toluene (150) | 40 | m-(p-benzoylphen-oxy)toluene | (4.9) |
| | | | m-(p-benzoylphen-oxy)benzyl chloride | (90.6) |
| | | | m-(p-benzoylphen-oxy)benzal chloride | (3.5) |
| | | | nucleus-substituted | (1.0) |
| 61 | m-(p-benzoylphen-oxy)toluene (150) | 80 | m-(p-benzoylphen-oxy)benzyl chloride | (2.8) |
| | | | m-(p-benzoylphen-oxy)benzal chloride | (92.7) |

TABLE 6-continued

| No. | Starting material (g) | Reac. time (min.) | Products | (yield, %) |
|---|---|---|---|---|
| Chlorination of phenoxytoluenes in the coexistence of triphenylphosphine | | | | |
| | | | m-(p-benzoylphenoxy)phenyl trichloromethane | (3.0) |
| | | | nucleus-substituted | (1.5) |
| 62 | m-(p-cyanophenoxy)toluene (109) | 80 | m-(p-cyanophenoxy)benzyl chloride | (8.2) |
| | | | m-(p-cyanophenoxy)benzal chloride | (85.6) |
| | | | m-(p-cyanophenoxy)phenyl trichloromethane | (3.9) |
| | | | nucleus-substituted | (2.3) |
| 63 | m-(p-nitrophenoxy)toluene (119) | 90 | m-(p-nitrophenoxy)benzyl chloride | (12.0) |
| | | | m-(p-nitrophenoxy)benzal chloride | (80.5) |
| | | | m-(p-nitrophenoxy)phenyl trichloromethane | (4.3) |
| | | | nucleus-substituted | (3.2) |
| 64 | m-(p-phenylphenoxy)toluene (135) | 40 | m-(p-phenylphenoxy)toluene | (3.2) |
| | | | m-(p-phenylphenoxy)benzyl chloride | (93.5) |
| | | | m-(p-phenylphenoxy)benzal chloride | (2.1) |
| | | | nucleus-substituted | (1.2) |
| 65 | m-(p-phenylphenoxy)toluene (135) | 90 | m-(p-phenylphenoxy)benzyl chloride | (1.1) |
| | | | m-(p-phenylphenoxy)benzal chloride | (93.0) |
| | | | m-(p-phenylphenoxy)phenyl trichloromethane | (4.8) |
| | | | nucleus-substituted | (1.1) |
| 66 | m-(p-benzylphenoxy)toluene (143) | 90 | m-(p-benzylphenoxy)benzyl chloride | (4.9) |
| | | | m-(p-benzylphenoxy)benzal chloride | (90.5) |
| | | | m-(p-benzylphenoxy)phenyl trichloromethane | (3.8) |
| | | | nucleus-substituted | (0.8) |
| 67 | m-(p-benzyloxyphenoxy)toluene (151) | 90 | m-(p-benzyloxyphenoxy)benzyl chloride | (5.5) |
| | | | m-(p-benzyloxyphenoxy)benzal chloride | (88.7) |
| | | | m-(p-benzyloxyphenoxy)phenyl trichloromethane | (4.3) |
| | | | nucleus-substituted | (1.5) |
| 68 | p-(m-tolyloxy)phenyl benzoate (158) | 80 | p-(m-chloromethylphenoxy)phenyl benzoate | (2.7) |
| | | | p-(m-dichloromethylphenoxy)phenyl benzoate | (90.9) |
| | | | p-(m-trichloromethylphenoxy)phenyl benzoate | (4.5) |
| | | | nucleus-substituted | (1.9) |
| 69 | m-(methoxyphenoxy)toluene (111) | 40 | m-(p-methoxyphenoxy)toluene | (8.4) |
| | | | m-(p-methoxyphenoxy)benzyl chloride | (87.1) |
| | | | m-(p-methoxyphenoxy)benzal chloride | (3.5) |
| | | | nucleus-substituted | (1.0) |
| 70 | m-(p-methoxycarbonyl phenoxy)toluene (126) | 40 | m-(p-methoxycarbonyl phenoxy)toluene | (6.9) |
| | | | m-(p-methoxycarbonyl phenoxy)benzyl chloride | (86.7) |
| | | | m-(p-methoxycarbonyl phenoxy)benzal chloride | (4.2) |
| | | | nucleus-substituted | (2.2) |

EXAMPLE 71

Table 7 shows the results of reactions which are conducted in a similar manner as in Example 54 with use of m-phenoxytoluene and typical phosphorus- or oxygen-containing compounds.

TABLE 7

Effect of phosphorus-containing and oxygen-containing compounds on the chlorination of m-phenoxytoluene

| No. | Phosphorus-containing or oxygen-containing compound | Reac. time (min.) | Products (Yield, %) (1) | (2) | (3) | (4) | (5) |
|---|---|---|---|---|---|---|---|
| 1 | Tri-n-butylphosphine | 40 | 9.3 | 89.1 | 1.1 | — | 0.5 |
| 2 | Tri-n-butylphosphine | 75 | — | 8.6 | 90.0 | 1.0 | 0.4 |
| 3 | Tri-n-octylphosphine | 80 | — | 8.2 | 89.2 | 1.6 | 1.0 |
| 4 | Tri-n-dodecylphosphine | 80 | — | 5.3 | 91.8 | 2.9 | — |
| 5 | n-Octadecyldiphenylphosphine | 80 | — | 5.5 | 92.4 | 1.2 | 0.9 |
| 6 | Mercaptoethyldiphenyl phosphine | 85 | — | 4.7 | 89.8 | 3.3 | 2.2 |
| 7 | Tricyclohexylphosphine | 80 | — | 5.9 | 90.7 | 2.4 | 1.0 |
| 8 | Dicyclohexyl 4-chlorophenylphosphine | 75 | — | 7.5 | 91.0 | 1.5 | — |
| 9 | Triisopropylphosphine sulfide | 80 | — | 5.8 | 89.3 | 4.2 | 0.7 |
| 10 | n-Hexadecyldiphenylphosphine sulfide | 40 | 10.1 | 88.6 | 1.3 | — | — |
| 11 | n-Hexadecyldiphenylphosphine sulfide | 80 | — | 4.5 | 90.8 | 3.2 | 1.5 |
| 12 | Triphenylphosphine oxide | 80 | — | 7.8 | 87.5 | 3.5 | 1.2 |
| 13 | Tri-n-dodecylphosphine oxide | 80 | — | 4.8 | 92.6 | 2.6 | — |
| 14 | N,N—Diethylhydrazinodiphenylphosphine oxide | 80 | — | 7.7 | 90.3 | 1.5 | 0.5 |
| 15 | 1-Phenyl-1-phosphacyclohexane | 80 | — | 5.2 | 91.1 | 3.1 | 0.6 |

TABLE 7-continued

Effect of phosphorus-containing and oxygen-containing compounds on the chlorination of m-phenoxytoluene

| No. | Phosphorus-containing or oxygen-containing compound | Reac. time (min.) | Products (Yield, %) (1) | (2) | (3) | (4) | (5) |
|---|---|---|---|---|---|---|---|
| 16 | n-Octadecyl diphenyl phosphite | 80 | — | 3.9 | 89.8 | 4.8 | 1.5 |
| 17 | Dicyclohexyl chloro phosphite | 80 | — | 2.9 | 91.9 | 4.0 | 1.2 |
| 18 | Di-n-octyl phosphite | 40 | 11.3 | 78.5 | 10.2 | — | — |
| 19 | Di-n-octyl phosphite | 80 | — | 10.3 | 85.2 | 3.5 | 1.0 |
| 20 | Diphenyl cyclohexyl phosphite | 80 | — | 8.8 | 89.1 | 2.1 | — |
| 21 | Triphenyl phosphite | 45 | 7.7 | 80.6 | 10.7 | — | 1.0 |
| 22 | Triphenyl phosphite | 80 | — | 5.0 | 91.7 | 3.3 | — |
| 23 | Tricyclohexyl phosphite | 75 | — | 8.1 | 85.3 | 4.5 | 2.1 |
| 24 | Diisopropyl chloro thiophosphite | 80 | — | 12.5 | 83.9 | 2.1 | 1.5 |
| 25 | Tricyclohexyl thiophosphite | 80 | — | 7.0 | 87.6 | 4.1 | 1.3 |
| 26 | Tri-n-dodecyl thiophosphite | 80 | — | 6.4 | 90.9 | 2.7 | — |
| 27 | Triphenyl thiophosphite | 45 | 15.3 | 80.5 | 4.2 | — | — |
| 28 | Triphenyl thiophosphite | 80 | — | 4.8 | 90.5 | 4.7 | — |
| 29 | Tris(dimethylamino)-phosphine | 80 | — | 7.4 | 87.6 | 1.9 | 3.1 |
| 30 | Phosphorus tripiperidide | 80 | — | 8.1 | 89.9 | 2.0 | — |
| 31 | Tris(di-n-butylamino)-phosphine | 80 | — | 14.3 | 80.1 | 3.4 | 2.2 |
| 32 | Phosphorus tri(N—methyl-anilide) | 80 | — | 14.2 | 81.3 | 2.1 | 2.4 |
| 33 | Diphenylphosphinic chloride | 75 | — | 12.3 | 82.2 | 4.1 | 1.4 |
| 34 | Cyclohexylphenylphosphino-thioic chloride | 80 | — | 12.9 | 80.5 | 5.0 | 1.6 |
| 35 | Di-n-butylphosphino-thioic acid | 80 | — | 10.5 | 84.1 | 4.2 | 1.2 |
| 36 | Isopropyl n-hexyl phosphinic acid | 80 | — | 7.7 | 85.3 | 4.8 | 2.2 |
| 37 | Dicyclohexylphosphino-dithioic acid | 80 | — | 13.4 | 78.8 | 4.8 | 3.0 |
| 38 | Methyl n-octyl n-hexyl phosphinate | 40 | 15.7 | 78.5 | 5.8 | — | — |
| 39 | Methyl n-octyl n-hexyl phosphinate | 80 | — | 11.4 | 84.5 | 3.1 | 1.0 |
| 40 | O—Methyl diisopropyl-phosphinothioate | 80 | — | 13.3 | 80.9 | 5.0 | 0.8 |
| 41 | Phenyl diethylphosphino-dithioate | 80 | — | 12.3 | 82.3 | 4.3 | 1.1 |
| 42 | Methyl dicyclohexyl phosphinate | 75 | — | 14.5 | 80.3 | 4.5 | 0.7 |
| 43 | Hexamethylene phosphoric triamide | 80 | — | 16.3 | 77.5 | 4.1 | 2.1 |
| 44 | Phenyl phosphonus dichloride | 75 | — | 16.0 | 78.6 | 4.0 | 1.4 |
| 45 | Cyclohexylphosphonic dichloride | 75 | — | 13.7 | 81.3 | 3.7 | 1.3 |
| 46 | S,S—Diethyl phenyl-phosphonodithioate | 45 | 12.2 | 80.2 | 7.6 | — | — |
| 47 | S,S—Diethyl phenyl-phosphonodithioate | 85 | — | 8.9 | 88.1 | 3.0 | — |
| 48 | Diethyl-n-butylphosphonate | 80 | — | 12.7 | 80.9 | 4.2 | 2.2 |
| 49 | O,O—Diethyl phenyl-phosphonothioate | 40 | 12.7 | 81.7 | 5.6 | — | — |
| 50 | O,O—Diethyl phenyl-phosphonothioate | 80 | — | 5.4 | 89.0 | 3.5 | 2.1 |
| 51 | O,S—Diethyl phenyl-phosphonothioate | 80 | — | 6.5 | 90.2 | 2.3 | 1.0 |
| 52 | S—Ethyl N,N—diethyl P—methyl phosphonoamide thioate | 80 | — | 6.4 | 87.6 | 4.5 | 1.5 |
| 53 | O—Ethyl phenyl phosphono-dithioate | 50 | 10.7 | 82.8 | 6.5 | — | — |
| 54 | O—Ethyl phenyl phosphono-dithioate | 90 | — | 4.5 | 92.3 | 3.2 | — |
| 55 | O—Ethyl S—phenyl phenyl-phosphonodithioate | 80 | — | 5.5 | 90.1 | 4.4 | — |
| 56 | 2,2'-Dichlorodiethyl ether | 80 | — | 19.5 | 77.0 | 3.5 | — |
| 57 | Di-n-butyl ether | 85 | — | 18.3 | 78.7 | 3.0 | — |
| 58 | Di-n-octyl ether | 80 | — | 15.5 | 80.3 | 3.1 | 1.1 |
| 59 | Di-n-octadecyl ether | 40 | 11.1 | 78.8 | 10.1 | — | — |
| 60 | Di-n-octadecyl ether | 80 | — | 6.6 | 87.2 | 4.7 | 1.5 |
| 61 | Diphenyl ether | 80 | — | 12.8 | 80.5 | 4.7 | 2.0 |
| 62 | Naphthyl ethyl ether | 80 | — | 8.3 | 85.3 | 3.6 | 2.8 |

TABLE 7-continued

Effect of phosphorus-containing and oxygen-containing compounds on the chlorination of m-phenoxytoluene

| No. | Phosphorus-containing or oxygen-containing compound | Reac. time (min.) | Products (Yield, %) (1) | (2) | (3) | (4) | (5) |
|---|---|---|---|---|---|---|---|
| 63 | Dicyclohexyl ether | 80 | — | 14.5 | 81.0 | 4.5 | — |
| 64 | 4-Pyridyl ethyl ether | 85 | — | 11.7 | 83.4 | 3.0 | 1.9 |
| 65 | p-Dioxane | 80 | — | 10.8 | 82.1 | 5.6 | 1.5 |
| 66 | Furan | 80 | — | 7.2 | 89.8 | 2.0 | 1.0 |
| 67 | Tetrahydrofuran | 80 | — | 5.3 | 90.2 | 4.5 | — |
| 68 | 15-Crown-5 | 40 | 15.6 | 80.9 | 3.0 | — | 0.5 |
| 69 | 15-Crown-5 | 80 | — | 6.9 | 90.5 | 1.6 | 1.0 |
| 70 | Dibenzo-18-Crown-6 | 40 | 16.2 | 80.0 | 2.6 | — | 1.2 |
| 71 | Dibenzo-18-Crown-6 | 80 | — | 14.1 | 81.6 | 1.6 | 2.7 |
| 72 | Isobutyl alcohol | 80 | — | 16.8 | 78.5 | 3.8 | 0.9 |
| 73 | n-Octyl alcohol | 80 | — | 8.6 | 85.9 | 4.0 | 1.5 |
| 74 | n-Tetradecyl alcohol | 80 | — | 10.9 | 83.6 | 3.4 | 2.1 |
| 75 | n-Octadecyl alcohol | 80 | — | 14.5 | 80.8 | 3.5 | 1.2 |
| 76 | m-Cresol | 70 | — | 16.8 | 75.8 | 3.2 | 4.2 |
| 77 | 2-(3-Tolyloxy)-3-methyl phenol | 70 | — | 14.9 | 77.8 | 3.5 | 3.8 |
| 78 | 2,6-Di-t-Butyl-4-methyl phenol | 70 | — | 10.5 | 82.7 | 3.3 | 3.5 |
| 79 | 2,2'-Methylenebis(4-methoxy-6-t-butyl phenol) | 70 | — | 9.1 | 83.3 | 3.6 | 4.0 |
| 80 | 4,4'-Thiobis(3-methyl-6-t-butyl phenol) | 75 | — | 8.8 | 84.5 | 2.9 | 3.8 |
| 81 | 4-Hydroxypyridine | 40 | 10.7 | 82.5 | 5.8 | — | 1.0 |
| 82 | 4-Hydroxypyridine | 80 | — | 7.4 | 85.9 | 3.1 | 3.6 |
| 83 | Cyclohexyl alcohol | 80 | — | 12.6 | 83.1 | 3.1 | 1.2 |
| 84 | Ethylene glycol | 85 | — | 12.3 | 83.1 | 3.7 | 0.9 |
| 85 | Ethylene dithioglycol | 85 | — | 12.7 | 84.2 | 2.1 | 1.0 |
| 86 | Ethylene glycol mono-n-butyl ether | 80 | — | 16.1 | 79.3 | 3.6 | 1.0 |
| 87 | Diethylene glycol mono-n-dodecyl ether | 80 | — | 12.7 | 80.9 | 4.9 | 1.5 |
| 88 | Propylene glycol diisopropionate | 80 | — | 13.0 | 83.1 | 2.8 | 1.1 |
| 89 | Tripropylene glycol monostearate | 80 | — | 6.6 | 86.8 | 3.8 | 2.8 |
| 90 | Ethylene glycol monophenyl ether | 80 | — | 13.2 | 82.2 | 3.7 | 0.9 |
| 91 | β-Cyclodextrin | 45 | 11.8 | 85.7 | 2.5 | — | — |
| 92 | β-Cyclodextrin | 80 | — | 5.2 | 89.2 | 4.1 | 1.5 |
| 93 | 1,5-Sorbitan monostearate | 45 | 14.1 | 80.3 | 5.6 | — | — |
| 94 | 1,5-Sorbitan monostearate | 85 | — | 12.1 | 83.5 | 3.5 | 0.9 |
| 95 | Glycerin monopalmitate | 85 | — | 13.0 | 82.8 | 3.0 | 1.2 |
| 96 | Bis(hydroxyethylthio-ethyl) ether | 40 | 12.0 | 80.7 | 6.3 | — | 1.0 |
| 97 | Bis(hydroxyethylthio-ethyl) ether | 80 | — | 10.6 | 85.9 | 2.8 | 0.7 |
| 98 | Bis(mercaptoethylthio-ethyl) ether | 85 | — | 5.9 | 90.2 | 3.1 | 0.8 |
| 99 | Bis(chloroethoxyethyl) ether | 80 | — | 16.0 | 80.1 | 2.8 | 1.1 |
| 100 | Bis(aminoethylthioethyl) ether | 85 | — | 9.7 | 85.5 | 3.8 | 1.0 |
| 101 | Ethylene dithioglycol hexamer | 85 | — | 8.4 | 88.9 | 1.8 | 0.9 |
| 102 | Polyethylene glycol Mn = 1,000 | 80 | — | 9.4 | 86.5 | 2.6 | 1.5 |
| 103 | Polypropylene glycol Mn = 3,000 | 80 | — | 10.1 | 85.0 | 3.7 | 1.2 |
| 104 | Polyoxyethylene 1,5-sorbitan monostearate Mn = 1,000 | 40 | 7.4 | 82.5 | 10.1 | — | — |
| 105 | Polyoxyethylene 1,5-sorbitan monostearate Mn = 1,000 | 80 | — | 10.8 | 84.6 | 2.5 | 2.1 |
| 106 | Polyoxyethylene glycerin monopalmitate Mn = 800 | 80 | — | 10.7 | 83.5 | 3.0 | 2.8 |
| 107 | Polyoxyethylene dodecyl ether Mn = 800 | 80 | — | 14.3 | 80.8 | 3.1 | 1.8 |
| 108 | Polyoxyethylene p-dodecyl-phenyl ether Mn = 700 | 80 | — | 14.7 | 81.7 | 2.3 | 1.3 |
| 109 | Polyoxyethylene lauryl-amine Mn = 600 | 80 | — | 11.9 | 84.4 | 2.7 | 1.0 |
| 110 | Polyoxyethylene lauryl- | 80 | — | 15.8 | 80.3 | 3.0 | 0.9 |

TABLE 7-continued

Effect of phosphorus-containing and oxygen-containing compounds on the chlorination of m-phenoxytoluene

| No. | Phosphorus-containing or oxygen-containing compound | Reac. time (min.) | Products (Yield, %) (1) | (2) | (3) | (4) | (5) |
|---|---|---|---|---|---|---|---|
| | amide $\overline{M}n$ = 600 | | | | | | |

(1) 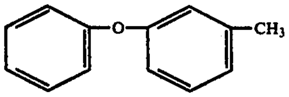

(2) 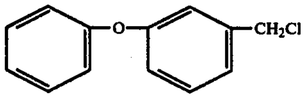

(3) 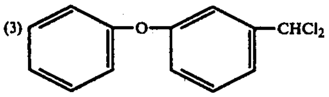

(4) 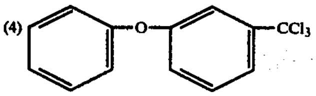

(5) 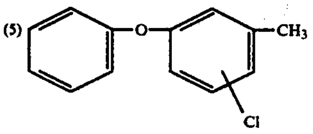

We claim:

1. A process for producing in high yield and high selectivity a chlorinated phenoxytoluene derivative represented by the formula

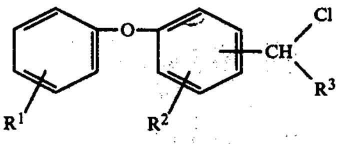 (1)

wherein $R^1$ and $R_2$ are the same or different and are each hydrogen, halogen, cyano, nitro, alkyl, alkoxyl, alkoxycarbonyl, halogenoalkyl, acyl, acyloxy, aryl, aralkyl or aralkyloxy, $R^3$ is hydrogen or chlorine, which comprises chlorinating at a temperature of 0° to 150° C. a phenoxytoluene derivative represented by the formula

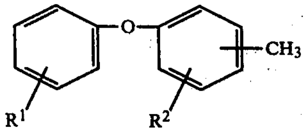 (2)

wherein $R^1$ and $R^2$ are same as above, with chlorine in an amount that provides said chlorinated phenoxytoluene derivative, in the presence of about 0.001 to 50 wt. % based on said phenoxytoluene derivative of at least one compound selected from the group consisting of nitrogen-containing compound, sulfur-containing compound, phosphorus-containing compound and oxygen-containing compound which is capable of forming a charge-transfer complex with chlorine, chlorine radical or organic halogen compound, together with about 0.001 to 20 wt. % based on said phenoxytoluene derivative of radical initiator and about 1 to 20 times the weight of said phenoxytoluene derivative of an organic halogen compound.

2. A process as defined in claim 1 wherein the nitrogen-containing compounds are those represented by the formulae

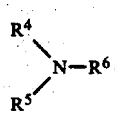 or $H_2N-R^7-NH_2$ in which $R^4$ to $R^6$ are each hydrogen, alkyl having 1 to 20 carbon atoms, hydroxyalkyl having 1 to 10 carbon atoms, cycloalkyl having 5 to 8 carbon atoms, aryl having 6 to 10 carbon atoms with or without a substituent, two or three of $R^4$ to $R^6$ may form a ring, $R^7$ is alkylene having 2 to 8 carbon atoms or arylene having 6 to 10 carbon atoms.

3. A process as defined in claim 1 wherein the sulfur-containing compounds are those represented by the formulae $R^8-SH$ $R^8-(S)_a-R^9$

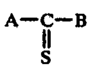 $R^{10}-N=C=S$

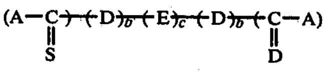

$[F-(S)_d]_e-(G-L)_f F$ $R^8$ and $R^9$ are each alkyl having 1 to 20 carbon atoms; cycloalkyl having 5 to 8 carbon atoms; aryl having 6 to 10 carbon atoms; heterocyclic group having nitrogen, sulfur, oxygen atom, etc, and $R^8$ and $R^9$ may conjointly form an alicyclic or heterocyclic ring, a is an integer of 1 to 8, A and B is $R^{11}$, $NR^{12}R^{13}$, $NR^{12}NR^{12}R^{13}$, $NR^{12}NCR^{12}R^{13}$, $SR^{12}$, $SNR^{12}R^{13}$, $SHNR^{12}R^{13}R^{14}$ or $OR^{14}$, $R^{10}$ to $R^{14}$ are hydrogen, alkyl having 1 to 20 carbon atoms aryl having 6 to 10 carbon atoms, alicyclic or heterocyclic ring and $R^{12}$ and $R^{13}$ or $R^{12}$ to $R^{14}$ may conjointly form a heterocyclic ring, $R^{12}$ and $R^{13}$ further include acyl having 1 to 20 carbon atoms with or without a substituent and $R^{11}$ does not include hydrogen, A and B may conjointly form an alicyclic or heterocyclic ring, D is $NR^{12}$, sulfur atom or oxygen atom, E is $R^{15}$, $R^{15}SR^{15}$, $R^{15}SO_2R^{15}$, $C(S)NHR^{15}NHC(S)$, $R^{15}NHC(S)NHR^{15}$, $R^{15}NR^{12}R^{15}$, $R^{15}C(O)R^{15}$ or $R^{15}C(S)R^{15}$, b is 0 or an integer of 1 to 4 but b is 1 when D is $NR^{12}$ or oxygen atom, c is 0 or 1, F is $R^{16}$, CN, $NR^{17}R^{18}$, $C(O)R^{17}$, $S(O)R^{17}$, $C(O)OR^{17}$, $C(O)NR^{17}R^{18}$, $C(O)SR^{17}$, $R^{19}C(O)OR^{17}$, $R^{19}C(O)NR^{17}R^{18}$, $R^{19}SR^{17}R^{19}NR^{17}R^{18}$, $R^{19}C(O)R^{17}$ or $HNR^{17}R^{17}R^{18}$, $R^{16}$ to $R^{18}$ are hydrogen; alkyl having 1 to 20 carbon atoms, aryl having 6 to 10 carbon atoms, alicyclic or heterocyclic froup with or without a substituent; but $R^{16}$ is alkyl, aryl or alicyclic group having a substituent when f is 0, $R^{19}$ is alkylene having 1 to 12 carbon atoms or arylene having 6 to 10 carbon atoms with or without a substituent, G is $R^{19}$, $R^{19}C(O)R^{19}$, $C(O)R^{19}C(O)$ or C(O), L is sulfur atom or $NR^{17}$, d is 1 to 8, e is 1 to 50 and f is 0 or 1 to 50, and F further includes $R^{19}OR^{17}$ and $R^{19}OR^{19}OR^{19}$ when d is other than 1.

4. A process as defined in claim 1 wherein the phosphorus-containing compounds are those represented by the formulae

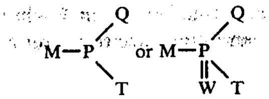

in which M, Q and T are hydrogen, halogen, $R^{20}$, $WR^{20}$ or $NR^{20}R^{21}$, $R^{20}$ and $R^{21}$ are the same or different and are hydrogen, alkyl having 1 to 20 carbon atoms; aryl having 6 to 10 carbon atoms; amino; alicyclic or heterocyclic ring, W is oxygen atom or sulfur atom, and M and Q, or Q and T may conjointly form an alicyclic or heterocyclic ring, and at least two of M, Q and T are organic group other than hydrogen.

5. A process as defined in claim 1 wherein the oxygen-containing compounds are those represented by the formulae $$R^{22}—OH,\ R^{22}—O—R^{23},\ X[(R^{24}—O)_{\overline{g}}(R^{25}—Z)_{\overline{h}}R^{24}—Y]_i$$

in which $R^{22}$ and $R^{23}$ are each alkyl having 1 to 20 carbon atoms, aryl having 6 to 10 carbon atoms, alicyclic or heterocyclic ring, and $R^{22}$ and $R^{23}$ may form an alicyclic, heterocyclic or large polyether ring, $R^{24}$ and $R^{25}$ are the same or different and are alkylene having 2 to 8 carbon atoms, X is oxygen atom, sulfur atom, alkoxyl, alkylamino or alkylamido, each having 1 to 20 carbon atoms and with or without a substituent, aryloxy having 6 to 10 carbon atoms, oxyalicyclic or oxyheterocyclic ring, each having or not having a substituent, Y is hydrogen, halogen, hydroxyl, mercapto, alkyl having 1 to 20 carbon atoms, carboxylalkyl having 2 to 20 carbon atoms or alkylamino having 1 to 20 carbon atoms, Z is oxygen atom or sulfur atom, g is 1 to 50, h is 0 to 25 and i is 1 to 6 but i is 2 when X is oxygen atom or sulfur atom.

6. A process as defined in claim 1 wherein the amount is about 0.01 to 30 wt % based on the starting phenoxytoluene derivative.

7. A process as defined in claim 1 wherein the organic halogen compounds are those represented by the formulae $CH_m(Hal)_{4-m}$, $CH_{m'}(Hal)_{3-m'}CH_{m'}(Hal)_{3-m'}$, $CH_{m''}(Hal)_{2-m''}=CH_{m''}(Hal)_{2-m''}$, 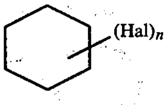

in which Hal means halogen atom, m is 0 or an integer of 1 to 3, m' is 0 or an integer of 1 to 2, m'' is 0 or 1, n is an integer of 1 to 6, or chlorinated paraffin.

8. A process as defined in claim 7 wherein the organic halogen compound is carbon tetrachloride, carbon tetrabromide, carbon tetraiodide, chloroform, bromoform, iodoform, methylene chloride, methylene bromide, dichloroethane, trichloroethane, tetrachloroethane, tetrachloroethylene or hexachlorocyclohexane.

9. A process as defined in claim 1 wherein the amount of 5 to 10 times the weight of the starting phenoxytoluene derivative.

10. A process as defined in claim 1 wherein the radical initiator is an azo compound or peroxide.

11. A process as defined in claim 10 wherein the radical initiator is azobisisobutyronitrile or benzoyl peroxide.

12. A process as defined in claim 1 wherein the amount is about 0.01 to 15 wt % of the starting phenoxytoluene derivative.

13. A process as defined in claim 1 wherein chlorine is blown into the reaction system in an amount of about 0.5 to 10 mole % per minute of the starting phenoxytoluene derivative.

14. A process as defined in claim 13 wherein the amount is about 2 to 5 mole % per minute of the starting phenoxytoluene derivative.

* * * * *